US006391542B1

(12) United States Patent
Anderson et al.

(10) Patent No.: US 6,391,542 B1
(45) Date of Patent: May 21, 2002

(54) COMPOSITIONS AND METHODS FOR TREATMENT OF HEPATITIS C VIRUS-ASSOCIATED DISEASES

(75) Inventors: Kevin P. Anderson, Carlsbad; Ronnie C. Hanecak, San Clemente, both of CA (US); Kazuya Hoshiko, Kumamoto (JP); Chikateru Nozaki, Kumamoto (JP); Tsukasa Nishihara, Kumamoto (JP); Hiroshi Nakatake, Kikuyo-machi (JP); Fukusaburo Hamada, Nishigoshi-machi (JP); Tatsuo Eto, Ohzu-machi (JP); Shinichi Furukawa, Koshi-machi (JP); Shoji Furasako, Tokyo (JP); Thomas W. Bruice, Carlsbad; Walter F. Lima, San Diego, both of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 08/650,093

(22) Filed: May 17, 1996

Related U.S. Application Data

(63) Continuation-in-part of application No. 08/452,841, filed on May 30, 1995, now abandoned, which is a continuation-in-part of application No. 08/397,220, filed on Mar. 9, 1995, now Pat. No. 6,284,458, which is a continuation-in-part of application No. 07/945,289, filed on Sep. 10, 1992, now abandoned.

(51) Int. Cl.$^7$ .......................... C12Q 1/68; C07H 21/04; C12N 15/85; C12P 19/34

(52) U.S. Cl. .......................... 435/6; 435/91.1; 435/325; 435/375; 536/23.1; 536/24.5

(58) Field of Search .................. 435/6, 91.1, 172.3, 435/325, 375; 514/44; 536/23.1, 24.5, 24.3

(56) References Cited

U.S. PATENT DOCUMENTS

| | | | |
|---|---|---|---|
| 4,806,463 A | 2/1989 | Goodchild et al. | 435/5 |
| 5,004,810 A | 4/1991 | Draper | 536/27 |
| 5,034,506 A | 7/1991 | Summerton et al. | 528/391 |
| 5,166,195 A | 11/1992 | Ecker | 514/44 |
| 5,194,428 A | 3/1993 | Agrawal et al. | 514/44 |
| 5,264,423 A | 11/1993 | Cohen et al. | 514/44 |
| 5,276,019 A | 1/1994 | Cohen et al. | 414/44 |

FOREIGN PATENT DOCUMENTS

| | | |
|---|---|---|
| CA | 2104649 | 8/1993 |
| EP | 318216 | 11/1988 |
| EP | 419182 | 9/1990 |
| WO | WO 94/08002 | 4/1994 |
| WO | WO 94/24864 | 11/1994 |

OTHER PUBLICATIONS

Choo et al., "Isolation of a cDNA Clone Derived from a Blood–Borne Non–A, Non–B Viral Hepatitis Genome", *Science* 1989, 244, 359–362.

Choo et al., "Genetic organization and diversity of the hepatitis C virus", *Proc. Natl. Acad. Sci.* 1991, 88, 2451–2455.

*BioWorld Today*, Apr. 29, 1994, p. 3.

Egholm et al., "Peptide Nucleic Acids (PNA). Oligonucleotide Analogues with an Achiral Peptide Backbone", *J. Am. Chem. Soc.* 1992, 114, 1895.

Egholm et al., "Recognition of Guanine and Adenine in DNA by Cytosine and Thymine Containing Peptide Nucleic Acids (PNA)", *J. Am. Chem. Soc.* 1992, 114, 9677.

Han et al., "Characterization of the terminal regions of hepatitis C viral RNA: Indentification of conserved sequences in the 5' untranslated region and poly(A) tails at the 3' end," *Proc. Natl. Acad. Sci.* 1991, 88, 1711–1715.

Inchauspe et al., "Genomic structure of the human prototype strain H of hepatitis C virus: Comparison with American and Japanese isolates," *Proc. Natl. Acad. Sci.* 1991, 88, 10292–10296.

Inoue, et al., "Synthesis and hybridization studies on two complementary nona(2'–O–methyl)ribonucleotides," *Nucleic Acids Research* 1991, 15:6131–6148.

Nielsen et al., "Sequence–selective recognition of DNA by strand displacement with a thymine–substituted polyamide," *Science* 1991, 254:1497–1500.

Sproat et al., "New synthetic routes to protected purine 2'–O–methylriboside–3'–O–phosphoramidites using a novel alkylation procedure," *Nucleic Acids Research* 18:41–49 (1990).

Takamizawa et al., "Structure and organization of the hepatitis C virus genome isolated from human carriers," *J. Virol.* 1991, 65:1105–1113.

Tsukiyama–Kohara et al., "Internal ribosome entry site within hepatitis C virus RNA," *J. Virol.* 1992, 66:1476–1483.

Vasseur et al., "Oligonucleosides: Synthesis of a Novel Methylhydroxylamine–Linked Nucleoside Dimer and Its Incorporation into Antisense Sequences", *J. Am. Chem. Soc.* 1992, 114, 4006–4007.

Wakita and Wands, "Specific Inhibition of Hepatitis C Virus Expression by Antisense Oliogdeoxynucleotides", *J. Biol. Chem.* 1994, 269, 14205–14210.

*Primary Examiner*—Andrew Wang
(74) *Attorney, Agent, or Firm*—Licata & Tyrrell P.C.

(57) ABSTRACT

Antisense oligonucleotides are provided which are complementary to and hybridizable with at least a portion of HCV RNA and which are capable of inhibiting the function of the HCV RNA. These oligonucleotides can be administered to inhibit the activity of Hepatitis C virus in vivo or in vitro. These compounds can be used either prophylactically or therapeutically to reduce the severity of diseases associated with Hepatitis C virus, and for diagnosis and detection of HCV and HCV-associated diseases. Methods of using these compounds are also disclosed.

8 Claims, 9 Drawing Sheets

FIG. 1

GCCAGCCCCCGAUUGGGGGCGACACUCCACCAUAGAUCACUCCCCUGUGAGGAACUACUGUCUUCACGCAG
AAAGCGUCUAGCCAUGGCGUUAGUAUGAGUGUCGUGCA<u>GCCUCCAGGACCCCCC</u>CUCCCGGGAGAGCCAUA
GUGGUCUGCGGAACCGGUGAGUACACCGGAAUUGCCAGGACGACCGGGUCCUUUCUUGGAUCAACCCGCTC
AAUGCCUGGAGAUUUGGGCGUGCCCCCGCGAGACUGCUAGCCGAGUAGUGUUGGGUCGCGAAAGGCCUUGU
GGUACUGCCUGAUAGGGUGCUUGCGAGUGCCCCGGGAGGUCUCGUAGACCGUGCACCAUGAGCACGAAUCC
UAAACCUCAAAGAAAAACCAAACGUAACACCAACCGCCGCCCACAGGAGGUCAAGUUCCCGGGCGGUGGUC
AGAUCGUUGGUGGAGUUUACCUGUUGCCGCGCAGGGGCCCCAGGUUGGGUGUGCGCGCGAUCAGGAAGACU
UCCGAGCGGUCGCAACCCCGUGGAAGGCGACAGCCUAUCCCCAAGGCUCGCCGGCCCGAGGGCAGGGCCUG
GGCUCAGCCCGGGUAUCCUUGGCCCCUCUAUGGCAAUGAGGGCAUGGGGUGGCAGGAUGGCUCCUGUCAC
CCCGCGGCUCCCGGCCUAGUUGGGGCCCCACGGACCCCCGGCGUAGG

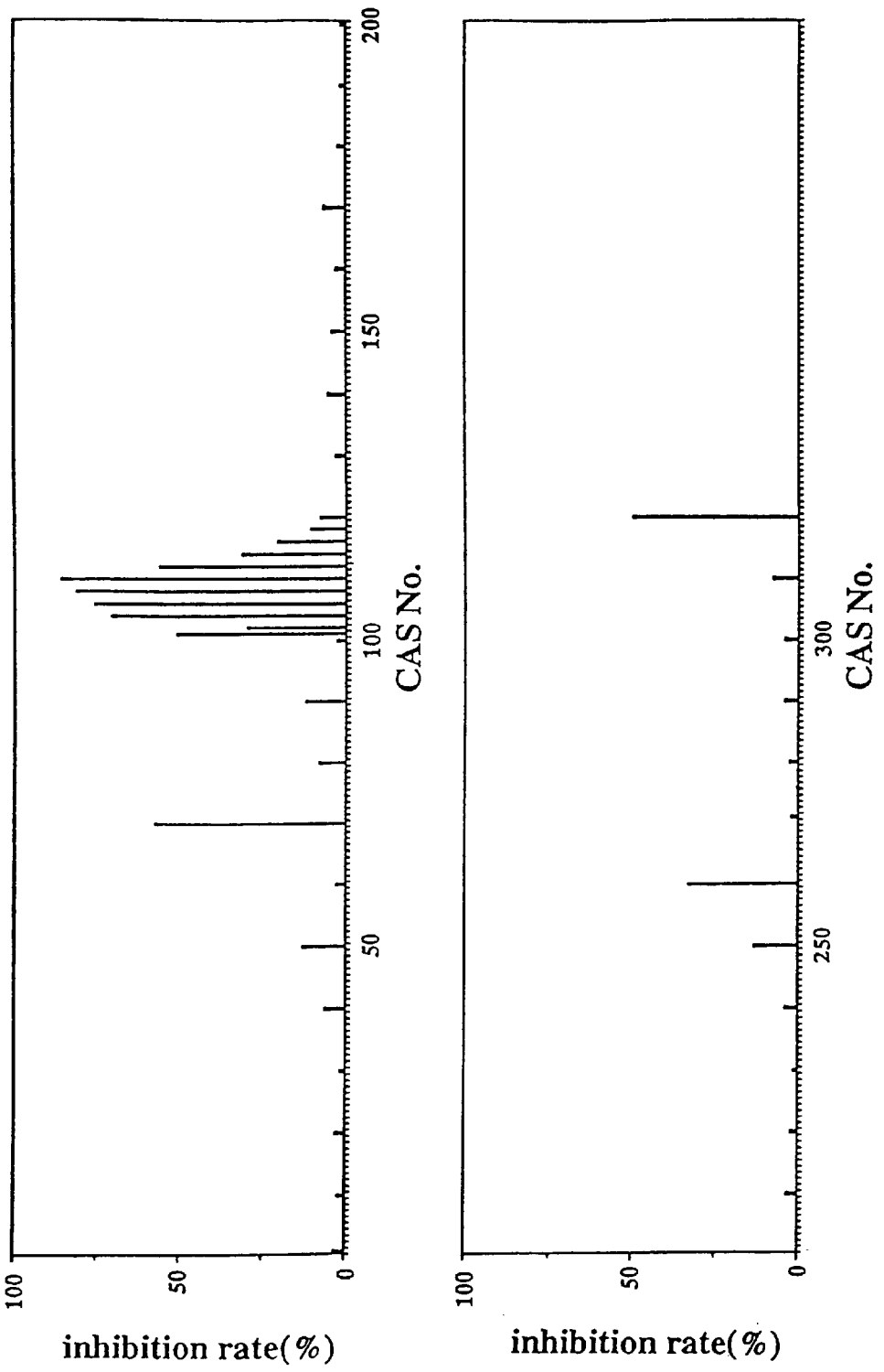

Inhibitory activity of 2'-o-methyl modified oligos and phosphodiester oligos from ISIS by in vitro core translation.
mRNA:oligos (1:5, molar ratio)

Influence of oligo. sequence and RNA length on *in vitro* translation

P=O

RNA709  : from Cla I-digested pGEM NCE1 plasmid
RNA1375 : from Bam HI-digested pGEM NCE1 plasmid Inhibition of HCV translation by the 2'-O-Methyl/P=O antisense oligonucleotides around C-loop and AUG codon Screening of the P=S oligos. by in vitro translation assay after treatment with RNase H Inhibitory activities of 2'OPro/P=O and 2'OMe/P=O oligos.

SEQUENCE LISTING (1) GENERAL INFORMATION:

(iii) NUMBER OF SEQUENCES: 118

(2) INFORMATION FOR SEQ ID NO: 1:

(i) SEQUENCE CHARACTERISTICS:
      (A) LENGTH: 21
      (B) TYPE: Nucleic Acid
      (C) STRANDEDNESS: Single
      (D) TOPOLOGY: Linear (iv) ANTI-SENSE: Yes (xi) SEQUENCE DESCRIPTION: SEQ ID NO: 1:

ATGGTGGAGT GTCGCCCCGT C      21

(2) INFORMATION FOR SEQ ID NO: 2:

(i) SEQUENCE CHARACTERISTICS:
      (A) LENGTH: 21
      (B) TYPE: Nucleic Acid
      (C) STRANDEDNESS: Single
      (D) TOPOLOGY: Linear (iv) ANTI-SENSE: Yes (xi) SEQUENCE DESCRIPTION: SEQ ID NO: 2:

GGAGTGATCT ATGGTGGAGT G                                              21

(2) INFORMATION FOR SEQ ID NO: 3:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 3:

GATTCGTGCT CATGGTGCAC G                                              21

(2) INFORMATION FOR SEQ ID NO: 4:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 4:

TCCAGGCATT GAGCGGGTTG A                                              21

(2) INFORMATION FOR SEQ ID NO: 5:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 5:

TGGCCTGGAG TGTTTATCTC C                                              21

(2) INFORMATION FOR SEQ ID NO: 6:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 6:

GGGGTAGGCA TCTACCTGCT C                                              21

(2) INFORMATION FOR SEQ ID NO: 7:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 7:

CGCCCCCATC AGGGGGCTGG C                                              21

(2) INFORMATION FOR SEQ ID NO: 8:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 8:

TTCATGGTGG AGTGTCGCCC C                                              21

(2) INFORMATION FOR SEQ ID NO: 9:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 9:

GTTCCTCACA GGGGAGTGAT T                                              21

(2) INFORMATION FOR SEQ ID NO: 10:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 10:

TACTAACGCC ATGGCTAGAC G                                              21

(2) INFORMATION FOR SEQ ID NO: 11:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 11:

CTATGGCTCT CCCGGGAGGG G                                              21

(2) INFORMATION FOR SEQ ID NO: 12:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 12:

CCACTATGGC TCTCCCGGGA G                                              21

(2) INFORMATION FOR SEQ ID NO: 13:

(i) SEQUENCE CHARACTERISTICS:
       (A) LENGTH: 21
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 13:

CGGTGTACTC ACCGGTTCCG C                                              21

(2) INFORMATION FOR SEQ ID NO: 14:

(i) SEQUENCE CHARACTERISTICS:
       (A) LENGTH: 21
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 14:

CTGGCAATTC CGGTGTACTC A                                              21

(2) INFORMATION FOR SEQ ID NO: 15:

(i) SEQUENCE CHARACTERISTICS:
       (A) LENGTH: 21
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 15:

GGGGCACGCC CAAATCTCCA G                                              21

(2) INFORMATION FOR SEQ ID NO: 16:

(i) SEQUENCE CHARACTERISTICS:
       (A) LENGTH: 21
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 16:

CCTTTCGCGA CCCAACACTA C                                              21

(2) INFORMATION FOR SEQ ID NO: 17:

(i) SEQUENCE CHARACTERISTICS:
       (A) LENGTH: 21
       (B) TYPE: Nucleic Acid
       (C) STRANDEDNESS: Single
       (D) TOPOLOGY: Linear (iv) ANTI-SENSE: Yes (xi) SEQUENCE DESCRIPTION: SEQ ID NO: 17:

CCCTATCAGG CAGTACCACA A                                              21

(2) INFORMATION FOR SEQ ID NO: 18:

(i) SEQUENCE CHARACTERISTICS:
       (A) LENGTH: 21
       (B) TYPE: Nucleic Acid (C) STRANDEDNESS: Single
        (D) TOPOLOGY: Linear (iv) ANTI-SENSE: Yes (xi) SEQUENCE DESCRIPTION: SEQ ID NO: 18:

CTCCCGGGGC ACTCGCAAGC A                                              21

(2) INFORMATION FOR SEQ ID NO: 19:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 19:

CATGGTGCAC GGTCTACGAG A                                              21

(2) INFORMATION FOR SEQ ID NO: 20:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 20:

GATTCGTGCT CATGGTGCAC G                                              21

(2) INFORMATION FOR SEQ ID NO: 21:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 21:

TTTAGGATTC GTGCTCATGG T                                              21

(2) INFORMATION FOR SEQ ID NO: 22:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 22:

GAGTGGTTAG CCCAATCTTC A                                              21

(2) INFORMATION FOR SEQ ID NO: 23:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 23:

TATTGGCCTG GAGTGGTTAG C                                              21

(2) INFORMATION FOR SEQ ID NO: 24:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 24:

AGGGAATGGC CTATTGGCCT G                                              21

(2) INFORMATION FOR SEQ ID NO: 25:

(i) SEQUENCE CHARACTERISTICS:
        (A) LENGTH: 686
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO : 25:

GCCAGCCCCC GAUUGGGGGC GACACUCCAC CAUAGAUCAC UCCCCUGUGA               50
GGAACUACUG UCUUCACGCA GAAAGCGUCU AGCCAUGGCG UUAGUAUGAG              100
UGUCGUGCAG CCUCCAGGAC CCCCCCUCCC GGGAGAGCCA UAGUGGUCUG              150
CGGAACCGGU GAGUACACCG GAAUUGCCAG GACGACCGGG UCCUUUCUUG              200
GAUCAACCCG CUCAAUGCCU GGAGAUUUGG GCGUGCCCCC GCGAGACUGC              250
UAGCCGAGUA GUGUUGGGUC GCGAAAGGCC UUGUGGUACU GCCUGAUAGG              300
GUGCUUGCGA GUGCCCCGGG AGGUCUCGUA GACCGUGCAC CAUGAGCACG              350
AAUCCUAAAC CUCAAAGAAA AACCAAACGU AACACCAACC GCCGCCCACA              400
GGAGGUCAAG UUCCCGGGCG GUGGUCAGAU CGUUGGUGGA GUUUACCUGU              450
UGCCGCGCAG GGGCCCCAGG UUGGGUGUGC GCGCGAUCAG GAAGACUUCC              500
GAGCGGUCGC AACCCCGUGG AAGGCGACAG CCUAUCCCCA AGGCUCGCCG              550
GCCCGAGGGC AGGGCCUGGG CUCAGCCCGG GUAUCCUUGG CCCCUCUAUG              600
GCAAUGAGGG CAUGGGGUGG GCAGGAUGGC UCCUGUCACC CCGCGGCUCC              650
CGGCCUAGUU GGGGCCCCAC GGACCCCCGG CGUAGG                            686

(2) INFORMATION FOR SEQ ID NO: 26:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 26:

GCCCCGAATC GGGGGCTGGC                                                20

(2) INFORMATION FOR SEQ ID NO: 27:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 27:

TGGAGTGTCG CCCCCAATCG                                          20

(2) INFORMATION FOR SEQ ID NO: 28:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 28:

TGATCTATGG TGGAGTGTCG                                          20

(2) INFORMATION FOR SEQ ID NO: 29:

(i) SEQUENCE CHARACTERISTICS:
        (A) LENGTH: 20
        (B) TYPE: Nucleic acid
        (C) STRANDEDNESS: Single
        (D) TOPOLOGY: Linear (iv) ANTI-SENSE: Yes (xi) SEQUENCE DESCRIPTION: SEQ ID NO: 29:

CACAGGGGAG TGATCTATGG                                          20

(2) INFORMATION FOR SEQ ID NO: 30:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 30:

AGTAGTTCCT CACAGGGGAG                                          20

(2) INFORMATION FOR SEQ ID NO: 31:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

GCGTGAAGAC AGTAGTTCCT                                          20

(2) INFORMATION FOR SEQ ID NO: 32:

(i) SEQUENCE CHARACTERISTICS:
        (A) LENGTH: 20
        (B) TYPE: Nucleic Acid
        (C) STRANDEDNESS: Single (D) TOPOLOGY: Linear (iv) ANTI-SENSE: Yes (xi) SEQUENCE DESCRIPTION: SEQ ID NO: 32:

GACGCTTTCT GCGTGAAGAC                                                           20

(2) INFORMATION FOR SEQ ID NO: 33:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 33:

GCCATGGCTA GACGCTTTCT                                                           20

(2) INFORMATION FOR SEQ ID NO: 34:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 34:

TCATACTAAC GCCATGGCTA                                                           20

(2) INFORMATION FOR SEQ ID NO: 35:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 35:

TGCACGACAC TCATACTAAC                                                           20

(2) INFORMATION FOR SEQ ID NO: 36:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 36:

TCCTGGAGGC TGCACGACAC                                                           20

(2) INFORMATION FOR SEQ ID NO: 37:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 37:

GGTCCTGGAG GCTGCACGAC                                               20

(2) INFORMATION FOR SEQ ID NO: 38:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 38:

GGGGTCCTGG AGGCTGCACG                                               20

(2) INFORMATION FOR SEQ ID NO: 39:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 39:

GGGGGGTCCT GGAGGCTGCA                                               20

(2) INFORMATION FOR SEQ ID NO: 40:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 40:

AGGGGGGGTC CTGGAGGCTG                                               20

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 41:

GGAGGGGGGG TCCTGGAGGC                                               20

(2) INFORMATION FOR SEQ ID NO: 42:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 42:

GGAGGGGGGG NCCTGGAGGC                                               20

(2) INFORMATION FOR SEQ ID NO: 43:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 43:

GGAGGGGGGG GCCTGGAGGC                                           20

(2) INFORMATION FOR SEQ ID NO: 44:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 44:

CGGGAGGGGG GGTCCTGGAG                                           20

(2) INFORMATION FOR SEQ ID NO: 45:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 45:

CCCGGGAGGG GGGGTCCTGG                                           20

(2) INFORMATION FOR SEQ ID NO: 46:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 46:

CTCCCGGGAG GGGGGGTCCT                                           20

(2) INFORMATION FOR SEQ ID NO: 47:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 47:

CTCTCCCGGG AGGGGGGGTC                                           20

(2) INFORMATION FOR SEQ ID NO: 48:

(i) SEQUENCE CHARACTERISTICS:

(A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 48:

GGCTCTCCCG GGAGGGGGGG                                              20

(2) INFORMATION FOR SEQ ID NO: 49:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 49:

AGACCACTAT GGCTCTCCCG                                              20

(2) INFORMATION FOR SEQ ID NO: 50:

(i) SEQUENCE CHARACTERISTICS:
        (A) LENGTH: 20
        (B) TYPE: Nucleic acid
        (C) STRANDEDNESS: Single
        (D) TOPOLOGY: Linear (iv) ANTI-SENSE: Yes (xi) SEQUENCE DESCRIPTION: SEQ ID NO: 50:

CCGGTTCCGC AGACCACTAT                                              20

(2) INFORMATION FOR SEQ ID NO: 51:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 51:

GGTGTACTCA CCGGTTCCGC                                              20

(2) INFORMATION FOR SEQ ID NO: 52:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 52:

TGGCAATTCC GGTGTACTCA                                              20

(2) INFORMATION FOR SEQ ID NO: 53:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 53:

CCGGTCGTCC TGGCAATTCC                                         20

(2) INFORMATION FOR SEQ ID NO: 54:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 54:

AAGAAAGGAC CCGGTCGTCC                                         20

(2) INFORMATION FOR SEQ ID NO: 55:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 55:

GGGTTGATCC AAGAAAGGAC                                         20

(2) INFORMATION FOR SEQ ID NO: 56:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 56:

GGCATTGAGC GGGTTGATCC                                         20

(2) INFORMATION FOR SEQ ID NO: 57:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 57:

CAAATCTCCA GGCATTGAGC                                         20

(2) INFORMATION FOR SEQ ID NO: 58:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 58:

GGGGCACGCC CAAATCTCCA                                          20

(2) INFORMATION FOR SEQ ID NO: 59:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 59:

CAGTCTCGCG GGGGCACGCC                                          20

(2) INFORMATION FOR SEQ ID NO: 60:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 60:

ACTCGGCTAG CAGTCTCGCG                                          20

(2) INFORMATION FOR SEQ ID NO: 61:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 61:

ACCCAACACT ACTCGGCTAG                                          20

(2) INFORMATION FOR SEQ ID NO: 62:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 62:

GCCTTTCGCG ACCCAACACT                                          20

(2) INFORMATION FOR SEQ ID NO: 63:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 63:

GTACCACAAG GCCTTTCGCG                                          20

(2) INFORMATION FOR SEQ ID NO: 64:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 64:

CTATCAGGCA GTACCACAAG                                      20

(2) INFORMATION FOR SEQ ID NO: 65:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 65:

CGCAAGCACC CTATCAGGCA                                      20

(2) INFORMATION FOR SEQ ID NO: 66:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 66:

CCGGGGCACT CGCAAGCACC                                      20

(2) INFORMATION FOR SEQ ID NO: 67:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 67:

ACGAGACCTC CCGGGGCACT                                      20

(2) INFORMATION FOR SEQ ID NO: 68:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 68:

TGCACGGTCT ACGAGACCTC                                      20

(2) INFORMATION FOR SEQ ID NO: 69:

(i) SEQUENCE CHARACTERISTICS:
        (A) LENGTH: 20

(B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 69:

GGTGCACGGT CTACGAGACC                                                    20

(2) INFORMATION FOR SEQ ID NO: 70:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 70:

ATGGTGCACG GTCTACGAGA                                                    20

(2) INFORMATION FOR SEQ ID NO: 71:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 71:

TCATGGTGCA CGGTCTACGA                                                    20

(2) INFORMATION FOR SEQ ID NO: 72:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 72:

GCTCATGGTG CACGGTCTAC                                                    20

(2) INFORMATION FOR SEQ ID NO: 73:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 73:

GTGCTCATGG TGCACGGTCT                                                    20

(2) INFORMATION FOR SEQ ID NO: 74:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 74:

TCGTGCTCAT GGTGCACGGT                                       20

(2) INFORMATION FOR SEQ ID NO: 75:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 75:

ATTCGTGCTC ATGGTGCACG                                       20

(2) INFORMATION FOR SEQ ID NO: 76:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 76:

GGATTCGTGC TCATGGTGCA                                       20

(2) INFORMATION FOR SEQ ID NO: 77:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 77:

TAGGATTCGT GCTCATGGTG                                       20

(2) INFORMATION FOR SEQ ID NO: 78:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 78:

TTTAGGATTC GTGCTCATGG                                       20

(2) INFORMATION FOR SEQ ID NO: 79:

(i) SEQUENCE CHARACTERISTICS:
              (A) LENGTH: 20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 79:

```
GGTTTAGGAT TCGTGCTCAT                                          20

(2) INFORMATION FOR SEQ ID NO: 80:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 80:

GAGGTTTAGG ATTCGTGCTC                                          20

(2) INFORMATION FOR SEQ ID NO: 81:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 81:

GAGGTTTAGG ATTNGTGCTC                                          20

(2) INFORMATION FOR SEQ ID NO: 82:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 82:

GNGGTTTNGG ATTNGTGCTC                                          20

(2) INFORMATION FOR SEQ ID NO: 83:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 83:

GNGGTTTNGG ANNNGTGCTC                                          20

(2) INFORMATION FOR SEQ ID NO: 84:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 84:

TTGAGGTTTA GGATTCGTGC                                          20

(2) INFORMATION FOR SEQ ID NO: 85:
```

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 85:

CTTTGAGGTT TAGGATTCGT                                          20

(2) INFORMATION FOR SEQ ID NO: 86:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 86:

TTCTTTGAGG TTTAGGATTC                                          20

(2) INFORMATION FOR SEQ ID NO: 87:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 87:

TTTTCTTTGA GGTTTAGGAT                                          20

(2) INFORMATION FOR SEQ ID NO: 88:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 88:

GTTTTTCTTT GAGGTTTAGG                                          20

(2) INFORMATION FOR SEQ ID NO: 89:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 89:

TGGTTTTTCT TTGAGGTTTA                                          20

(2) INFORMATION FOR SEQ ID NO: 90:

(i) SEQUENCE CHARACTERISTICS:
        (A) LENGTH: 20
        (B) TYPE: Nucleic Acid (C) STRANDEDNESS: Single
            (D) TOPOLOGY: Linear (iv) ANTI-SENSE: Yes (xi) SEQUENCE DESCRIPTION: SEQ ID NO: 90:

TTTGGTTTTT CTTTGAGGTT                                              20

(2) INFORMATION FOR SEQ ID NO: 91:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 91:

CGTTTGGTTT TTCTTTGAGG                                              20

(2) INFORMATION FOR SEQ ID NO: 92:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 92:

CAAGGCCTTT CGCGACCCAA                                              20

(2) INFORMATION FOR SEQ ID NO: 93:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 93:

CATGGTGCAC GGTCTACGAG                                              20

(2) INFORMATION FOR SEQ ID NO: 94:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 94:

GTTACGTTTG GTTTTTCTTT                                              20

(2) INFORMATION FOR SEQ ID NO: 95:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 95:

TGGTGTTACG TTTGGTTTTT                                                    20

(2) INFORMATION FOR SEQ ID NO: 96:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 96:

GGTTGGTGTT ACGTTTGGTT                                                    20

(2) INFORMATION FOR SEQ ID NO: 97:

(i) SEQUENCE CHARACTERISTICS:
        (A) LENGTH: 14
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 97:

GCCUCCAGGA CCCC                                                          14

(2) INFORMATION FOR SEQ ID NO: 98:

(i) SEQUENCE CHARACTERISTICS:
        (A) LENGTH: 26
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 98:

CGUGCAGCCU CCAGGACCCC CCCUCC                                             26

(2) INFORMATION FOR SEQ ID NO: 99:

(i) SEQUENCE CHARACTERISTICS:
        (A) LENGTH: 18
        (B) TYPE: Nucleic acid
        (C) STRANDEDNESS: Single
        (D) TOPOLOGY: Linear (iv) ANTI-SENSE: Yes (xi) SEQUENCE DESCRIPTION: SEQ ID NO: 99:

TCACAACCCA GCGCTTTC                                                      18

(2) INFORMATION FOR SEQ ID NO: 100:

(i) SEQUENCE CHARACTERISTICS:
        (A) LENGTH: 17
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 100:

TCACAACCCA GCGCTTT                                                       17

(2) INFORMATION FOR SEQ ID NO: 101:

(i) SEQUENCE CHARACTERISTICS:
        (A) LENGTH: 15
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 101:

TCACAACCCA GCGCT                                                    15

(2) INFORMATION FOR SEQ ID NO: 102:

(i) SEQUENCE CHARACTERISTICS:
        (A) LENGTH: 18
        (B) TYPE: Nucleic acid
        (C) STRANDEDNESS: Single
        (D) TOPOLOGY: Linear (iv) ANTI-SENSE: Yes (xi) SEQUENCE DESCRIPTION: SEQ ID NO: 102:

ACAACCCAGC GCTTTCCG                                                 18

(2) INFORMATION FOR SEQ ID NO: 103:

(i) SEQUENCE CHARACTERISTICS:
        (A) LENGTH: 17
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 103:

CAACCCAGCG CTTTCCG                                                  17

(2) INFORMATION FOR SEQ ID NO: 104:

(i) SEQUENCE CHARACTERISTICS:
        (A) LENGTH: 15
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 104:

ACCCAGCGCT TTCCG                                                    15

(2) INFORMATION FOR SEQ ID NO: 105:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 105:

CACAACCCAG CGCTTTCC                                                 18

(2) INFORMATION FOR SEQ ID NO: 106:

```
    (i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 106:

ACAACCCAGC GCTTTC                                                       16

(2) INFORMATION FOR SEQ ID NO: 107:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 107:

CCTTTCGCGA CCCAACACTA                                                   20

(2) INFORMATION FOR SEQ ID NO: 108:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 108:

GTGCTCATGG TGCACGGT                                                     18

(2) INFORMATION FOR SEQ ID NO: 109:

(i) SEQUENCE CHARACTERISTICS:
        (A) LENGTH: 17
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 109:

GTGCTCATGG TGCACGG                                                      17

(2) INFORMATION FOR SEQ ID NO: 110:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 110:

GTGCTCATGG TGCACG                                                       16

(2) INFORMATION FOR SEQ ID NO: 111:

(i) SEQUENCE CHARACTERISTICS:
        (A) LENGTH: 15
        (B) TYPE: Nucleic Acid
        (C) STRANDEDNESS: Single
```

(D) TOPOLOGY: Linear (iv) ANTI-SENSE: Yes (xi) SEQUENCE DESCRIPTION: SEQ ID NO: 111:

GTGCTCATGG TGCAC                                                            15

(2) INFORMATION FOR SEQ ID NO: 112:

(i) SEQUENCE CHARACTERISTICS:
            (A) LENGTH: 10
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 112:

GTGCTCATGG                                                                  10

(2) INFORMATION FOR SEQ ID NO: 113:

(i) SEQUENCE CHARACTERISTICS:
            (A) LENGTH: 18
            (B) TYPE: Nucleic acid
            (C) STRANDEDNESS: Single
            (D) TOPOLOGY: Linear (iv) ANTI-SENSE: Yes (xi) SEQUENCE DESCRIPTION: SEQ ID NO: 113:

GCTCATGGTG CACGGTCT                                                         18

(2) INFORMATION FOR SEQ ID NO: 114:

(i) SEQUENCE CHARACTERISTICS:
            (A) LENGTH: 17
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 114:

CTCATGGTGC ACGGTCT                                                          17

(2) INFORMATION FOR SEQ ID NO: 115:

(i) SEQUENCE CHARACTERISTICS:
            (A) LENGTH: 15
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 115:

CATGGTGCAC GGTCT                                                            15

(2) INFORMATION FOR SEQ ID NO: 116:

(i) SEQUENCE CHARACTERISTICS:
            (A) LENGTH: 10
            (B) TYPE: Nucleic Acid
            (C) STRANDEDNESS: Single
            (D) TOPOLOGY: Linear (iv) ANTI-SENSE: Yes -continued

```
    (xi) SEQUENCE DESCRIPTION: SEQ ID NO: 116:

TGCACGGTCT                                                      10

(2) INFORMATION FOR SEQ ID NO: 117:

(i) SEQUENCE CHARACTERISTICS:
        (A) LENGTH: 18
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 117:

TGCTCATGGT GCACGGTC                                             18

(2) INFORMATION FOR SEQ ID NO: 118:

(i) SEQUENCE CHARACTERISTICS:
        (A) LENGTH: 16
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 118:

GCTCATGGTG CACGGT                                               16
```

COMPOSITIONS AND METHODS FOR TREATMENT OF HEPATITIS C VIRUS-ASSOCIATED DISEASES

INTRODUCTION

This application is a continuation-in-part of U.S. Ser. No. 08/452,841, filed May 30, 1995, now abandoned which is a continuation-in-part of U.S. Ser. No. 08/397,220, filed Mar. 9, 1995, now U.S. Pat. No. 6,284,458 which is a continuation-in-part of U.S. Ser. No. 07/945,289, filed Sep. 10, 1992, now abandoned.

FIELD OF THE INVENTION

This invention relates to the design and synthesis of antisense oligonucleotides which can be administered to inhibit the activity of Hepatitis C virus in vivo or in vitro and to prevent or treat Hepatitis C virus-associated disease. These compounds can be used either prophylactically or therapeutically to reduce the severity of diseases associated with Hepatitis C virus. These compounds can also be used for detection of Hepatitis C virus and diagnosis of Hepatitis C virus-associated diseases. Oligonucleotides which are specifically hybridizable with Hepatitis C virus RNA targets and are capable of inhibiting the function of these RNA targets are disclosed. Methods of using these compounds are also disclosed.

BACKGROUND OF THE INVENTION

The predominant form of hepatitis currently resulting from transfusions is not related to the previously characterized Hepatitis A virus or Hepatitis B virus and has, consequently, been referred to as Non-A, Non-B Hepatitis (NANBH). NANBH currently accounts for over 90% of cases of post-transfusion hepatitis. Estimates of the frequency of NANBH in transfusion recipients range from 5%–13% for those receiving volunteer blood, or 25–54% for those receiving blood from commercial sources.

Acute NANBH, while often less severe than acute disease caused by Hepatitis A or Hepatitis B viruses, can lead to severe or fulminant hepatitis. Of greater concern, progression to chronic hepatitis is much more common after NANBH than after either Hepatitis A or Hepatitis B infection. Chronic NANBH has been reported in 10%–70% of infected individuals. This form of hepatitis can be transmitted even by asymptomatic patients, and frequently progresses to malignant disease such as cirrhosis and hepatocellular carcinoma. Chronic active hepatitis, with or without cirrhosis, is seen in 44%–90% of posttransfusion hepatitis cases. Of those patients who developed cirrhosis, approximately one-fourth died of liver failure.

Chronic active NANBH is a significant problem to hemophiliacs who are dependent on blood products; 5%–11% of hemophiliacs die of chronic end-stage liver disease. Cases of NANBH other than those traceable to blood or blood products are frequently associated with hospital exposure, accidental needle stick, or tattooing. Transmission through close personal contact also occurs, though this is less common for NANBH than for Hepatitis B.

The causative agent of the majority of NANBH has been identified and is now referred to as Hepatitis C Virus (HCV). Houghton et al., EP Publication 318,216; Choo et al., *Science* 1989, 244, 359–362. Based on serological studies using recombinant DNA-generated antigens it is now clear that HCV is the causative agent of most cases of post-transfusion NANBH. The HCV genome is a positive or plus-strand RNA genome. EP Publication 318,216 (Houghton et al.) discloses partial genomic sequences of HCV-1, and teaches recombinant DNA methods of cloning and expressing HCV sequences and HCV polypeptides, techniques of HCV immunodiagnostics, HCV probe diagnostic techniques, anti-HCV antibodies, and methods of isolating new HCV sequences. Houghton et al. also disclose additional HCV sequences and teach application of these sequences and polypeptides in immunodiagnostics, probe diagnostics, anti-HCV antibody production, PCR technology and recombinant DNA technology. The concept of using antisense polynucleotides as inhibitors of viral replication is disclosed, but no specific targets are taught. Oligomer probes and primers based on the sequences disclosed are also provided. EP Publication 419,182 (Miyamura et al.) discloses new HCV isolates J1 and J7 and use of sequences distinct from HCV-1 sequences for screens and diagnostics.

The only treatment regimen shown to be effective for the treatment of chronic NANBH is interferon-α. Most NANBH patients show an improvement of clinical symptoms during interferon treatment, but relapse is observed in at least half of patients when treatment is interrupted. Significant improvements in antiviral therapy are therefore greatly desired. An obvious need exists for a clinically effective antiviral therapy for acute and chronic HCV infections. Such an antiviral would also be useful for preventing the development of HCV-associated disease, for example for individuals accidently exposed to blood products containing infectious HCV. There is also a need for research reagents and diagnostics which are able to differentiate HCV-derived hepatitis from hepatitis caused by other agents and which are therefore useful in designing appropriate therapeutic regimes.

Antisense Oligonucleotides

Oligonucleotides are commonly used as research reagents and diagnostics. For example, antisense oligonucleotides, which, by nature, are able to inhibit gene expression with exquisite specificity, are often used by those of ordinary skill to elucidate the function of particular genes, for example to determine which viral genes are essential for replication, or to distinguish between the functions of various members of a biological pathway. This specific inhibitory effect has, therefore, been exploited for research use. This specificity and sensitivity is also harnessed by those of skill in the art for diagnostic uses. Viruses capable of causing similar hepatic symptoms can be easily and readily distinguished in patient samples, allowing proper treatment to be implemented. Antisense oligonucleotide inhibition of viral activity in vitro is useful as a means to determine a proper course of therapeutic treatment. For example, before a patient suspected of having an HCV infection is contacted with an oligonucleotide composition of the present invention, cells, tissues or a bodily fluid from the patient can be contacted with the oligonucleotide and inhibition of viral RNA function can be assayed. Effective in vitro inhibition of HCV RNA function, routinely assayable by methods such as Northern blot or RT-PCR to measure RNA replication, or Western blot or ELISA to measure protein translation, indicates that the infection will be responsive to the oligonucleotide treatment.

Oligonucleotides have also been employed as therapeutic moieties in the treatment of disease states in animals and man. For example, workers in the field have now identified antisense, triplex and other oligonucleotide compositions which are capable of modulating expression of genes implicated in viral, fungal and metabolic diseases. As examples, U.S. Pat. No. 5,166,195 issued Nov. 24, 1992, provides oligonucleotide inhibitors of HIV. U.S. Pat. No. 5,004,810, issued Apr. 2, 1991, provides oligomers capable of hybridizing to herpes simplex virus Vmw65 mRNA and inhibiting replication. U.S. Pat. No. 5,194,428, issued Mar. 16, 1993, provides antisense oligonucleotides having antiviral activity against influenzavirus. U.S. Pat. No. 4,806,463, issued Feb. 21, 1989, provides antisense oligonucleotides and methods using them to inhibit HTLV-III replication. U.S. Pat. No. 5,276,019 and U.S. Pat. No. 5,264,423 (Cohen et al.) are directed to phosphorothioate oligonucleotide analogs used to prevent replication of foreign nucleic acids in cells. Antisense oligonucleotides have been safely and effectively administered to humans and clinical trials of several antisense oligonucleotide drugs are presently underway. The phosphorothioate oligonucleotide, ISIS 2922, has been shown to be effective against cytomegalovirus retinitis in AIDS patients. *BioWorld Today*, Apr. 29, 1994, p. 3. It is thus established that oligonucleotides can be useful drugs for treatment of cells and animal subjects, especially humans.

Seki et al. have disclosed antisense compounds complementary to specific defined regions of the HCV genome. Canadian patent application 2,104,649.

Hang et al. have disclosed antisense oligonucleotides complementary to the 5' untranslated region of HCV for controlling translation of HCV proteins, and methods of using them. WO 94/08002.

Blum et al. have disclosed antisense oligonucleotides complementary to an RNA complementary to a portion of a hepatitis viral genome which encodes the terminal protein region of the viral polymerase, and methods of inhibiting replication of a hepatitis virus using such oligonucleotides. WO 94/24864.

Wakita and Wands have used sense and antisense oligonucleotides to determine the role of the 5' end untranslated region in the life cycle of HCV. Antisense oligonucleotides targeted to three regions of the 5' untranslated region and one region of the core protein coding region effectively blocked in vitro translation of HCV protein, suggesting that these domains may be critical for HCV translation. *J. Biol. Chem.* 1994, 269, 14205–14210.

BRIEF DESCRIPTION OF THE DRAWINGS

FIG. 1 is the sequence of nucleotides 1–686 comprising the entire 5'-untranslated region (nucleotides 1–341) and a 145-nucleotide core region sequence of HCV RNA.

FIG. 2 is a bar graph showing inhibition of HCV core protein translation by antisense oligonucleotides complementary to the region from nucleotide 1 to 350 of HCV RNA.

SUMMARY OF THE INVENTION

Figure 3:
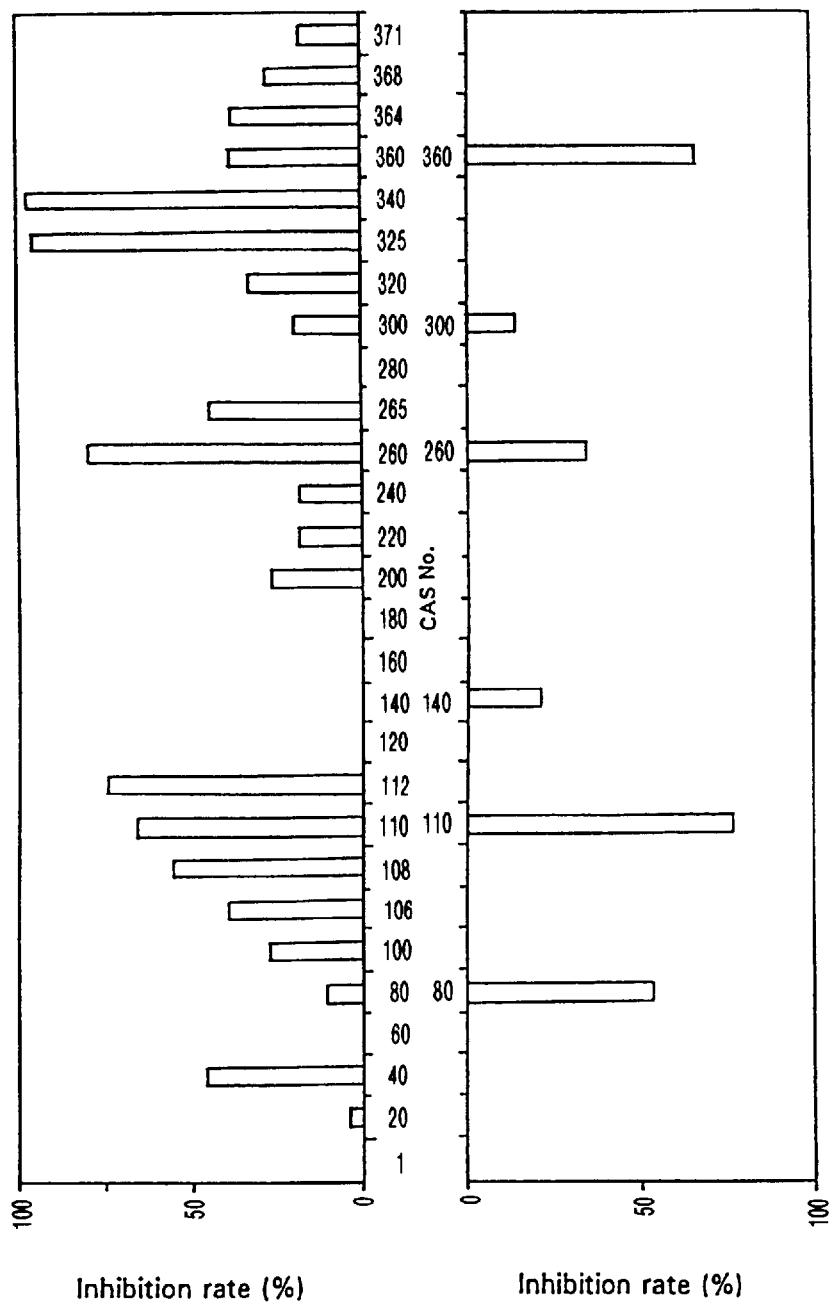
FIG. 3 is a bar graph showing inhibition of HCV core protein translation by 2'-O-methylated antisense oligonucleotides and selected unmodified oligonucleotides of the same sequence.

In accordance with the present invention, compositions and methods for modulating the effects of HCV infection are provided. Oligonucleotides which are complementary to, and specifically hybridizable with, selected sequences of HCV RNA and which are capable of inhibiting the function of the HCV RNA are provided. The HCV 5' end hairpin loop, 5' end 6-base-pair repeats, 5' end untranslated region, polyprotein translation initiation codon, core protein coding region, ORF 3 translation initiation codon, 3'-untranslated region, 3' end palindrome region, R2 sequence and 3' end hairpin loop are preferred targets. Methods for diagnosing or treating disease states by administering oligonucleotides, either alone or in combination with a pharmaceutically acceptable carrier, to animals suspected of having HCV-associated diseases are also provided.

DETAILED DESCRIPTION OF THE INVENTION

Several regions of the HCV genome have been identified as antisense targets in the present invention. The size of the HCV genome is approximately 9400 nucleotides, with a single translational reading frame encoding a polyprotein which is subsequently processed to several structural and non-structural proteins. It should be noted that sequence availability and nucleotide numbering schemes vary from strain to strain. The 5' untranslated region (5' UTR) or 5' noncoding region (5' NCR) of HCV consists of approximately 341 nucleotides upstream of the polyprotein translation initiation codon. A hairpin loop present at nucleotides 1–22 at the 5' end of the genome (HCV-1) identified herein as the "5' end hairpin loop" is believed to serve as a recognition signal for the viral replicase or nucleocapsid proteins. Han et al., *Proc. Natl. Acad. Sci.* 1991, 88, 1711–1715. The 5' untranslated region is believed to have a secondary structure which includes six stem-loop structures, designated loops A–F. Loop A is present at approximately nucleotides 13–50, loop B at approximately nucleotides 51–88, loop C at approximately nucleotides 100–120, loop D at approximately nucleotides 147–162, loop E at approximately nucleotides 163–217, and loop F at approximately nucleotides 218–307. Tsukiyama-Kohara et al., *J. Virol.* 1992, 66, 1476–1483. These structures are well conserved between the two major HCV groups.

Three small (12–16 amino acids each) open reading frames (ORFs) are located in the 5'-untranslated region of HCV RNA. These ORFs may be involved in control of translation. The ORF 3 translation initiation codon as denominated herein is found at nucleotides 315–317 of HCV-1 according to the scheme of Han et al., *Proc. Natl. Acad. Sci.* 1991, 88, 1711–1715; and at nucleotides −127 to −125 according to the scheme of Choo et al., *Proc. Natl. Acad. Sci.* 1991, 88, 2451–2455.

The polyprotein translation initiation codon as denominated herein is an AUG sequence located at nucleotides 342–344 of HCV-1 according to Han et al., *Proc. Natl. Acad. Sci.* 1991, 88, 1711–1715 or at nucleotide 1–3 according to the HCV-1 numbering scheme of Choo et al., *Proc. Natl. Acad. Sci.* 1991, 88, 2451–2455. Extending downstream (toward 3' end) from the polyprotein AUG is the core protein coding region.

The 3' untranslated region, as denominated herein, consists of nucleotides downstream of the polyprotein translation termination site (ending at nt 9037 according to Choo et al.; nt 9377 according to schemes of Han and Inchauspe). Nucleotides 9697–9716 (numbering scheme of Inchauspe for HCV-H) at the 3' terminus of the genome within the 3' untranslated region can be organized into a stable hairpin loop structure identified herein as the 3' hairpin loop. A short nucleotide stretch (R2) immediately upstream (nt 9691–9696 of HCV-H) of the 3' hairpin, and denominated herein "the R2 sequence", is thought to play a role in cyclization of the viral RNA, possibly in combination with a set of 5' end 6-base-pair repeats of the same sequence at nt 23–28 and 38–43. (Inchauspe et al., *Proc. Natl. Acad. Sci.* 1991, 88, 10292–10296) is identified herein as "5' end 6-base-pair repeat". Palindrome sequences present near the 3' end of the genome (nucleotides 9312–9342 according to the scheme of Takamizawa et al., *J. Virol.* 1991, 65, 1105–1113) are capable of forming a stable secondary structure. This is referred to herein as the 3' end palindrome region.

Antisense Oligonucleotides

The present invention employs oligonucleotides 5 to 50 nucleotides in length which are specifically hybridizable with hepatitis C virus RNA and are capable of inhibiting the function of the HCV RNA. In preferred embodiments, oligonucleotides are targeted to the 5' end hairpin loop, 5' end 6-base-pair repeats, 5' end untranslated region, polyprotein translation initiation codon, core protein coding region, ORF 3 translation initiation codon, 3'-untranslated region, 3' end palindrome region, R2 sequence and 3' end hairpin loop region of HCV RNA. This relationship between an oligonucleotide and the nucleic acid sequence to which it is targeted is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid (RNA or DNA) from an infectious agent. In the present invention, the target is the 5' end hairpin loop, 5' end 6-base-pair repeats, ORF 3 translation initiation codon (all of which are contained within the 5' UTR), polyprotein translation initiation codon, core protein coding region (both of which are contained within the coding region), 3' end palindrome region, R2 sequence or 3' end hairpin loop (all of which are contained within the 3' UTR) of HCV RNA. The targeting process also includes determination of a site or sites within the nucleic acid sequence for the oligonucleotide interaction to occur such that the desired effect, i.e., inhibition of HCV RNA function, will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of HCV RNA function is presently the preferred form of modulation in the present invention. The oligonucleotides are able to inhibit the function of viral RNA by interfering with its replication, transcription into mRNA, translation into protein, packaging into viral particles or any other activity necessary to its overall biological function. The failure of the RNA to perform all or part of its function results in failure of all or a portion of the normal life cycle of the virus. This inhibition can be measured, in samples derived from either in vitro or in vivo (animal) systems, in ways which are routine in the art, for example by RT-PCR or Northern blot assay of HCV RNA levels or by in vitro translation, Western blot or ELISA assay of protein expression as taught in the examples of the instant application. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers or polymers comprising non-naturally occurring monomers, or portions thereof, which function similarly. Such modified or substituted oligonucleotides are often preferred over native forms because of properties such as, for example, enhanced cellular uptake, increased stability in the presence of nucleases, or enhanced target affinity. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A number of modifications have also been shown to increase binding (affinity) of the oligonucleotide to its target. Affinity of an oligonucleotide for its target is routinely determined by measuring the Tm of an oligonucleotide/target pair, which is the temperature at which the oligonucleotide and target dissociate. Dissociation is detected spectrophotometrically. The higher the Tm, the greater the affinity of the oligonucleotide for the target. In some cases, oligonucleotide modifications which enhance target binding affinity are also, independently, able to enhance nuclease resistance.

Specific examples of some preferred oligonucleotides envisioned for this invention may contain phosphorothioates (P=S), phosphotriesters, methyl phosphonates, short chain alkyl or cycloalkyl intersugar linkages or short chain heteroatomic or heterocyclic intersugar ("backbone") linkages at one or more positions instead of the native phosphodiester (P=O) backbone. Most preferred are phosphorothioates and those with $CH_2$—NH—O—$CH_2$, $CH_2$—N($CH_3$)—O—$CH_2$

[known as a methylene(methylimino) or MMI backbone], $CH_2$—O—$N(CH_3)$—$CH_2$, $CH_2$—$N(CH_3)$—$N(CH_3)$—$CH_2$ and O—$N(CH_3)$ —$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. : 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Oligonucleotides containing one or more PNA, MMI or P=S backbone linkages are presently more preferred. Other preferred oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N—alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a reporter group; an intercalator; a group for improving the pharmacokinetic properties of an oligonucleotide; or a group for improving the pharmacodynamic properties of an oligonucleotide and other substituents having similar properties. Presently preferred modifications include 2'-methoxyethoxy (2'-O—$CH_2CH_2OCH_3$), 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group. Other preferred embodiments may include at least one modified base form or "universal base" such as inosine. Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one preferred embodiment, a chimeric oligonucleotide comprises at least one region modified to increase target binding affinity, and, usually, a region that acts as a substrate for RNAse H. Affinity of an oligonucleotide for its target (in this case a nucleic acid encoding HCV RNA) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase HCV RNA binding affinity comprises at least one nucleotide modified at the 2' position of the sugar, most preferably a 2'-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of HCV RNA function. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. In some cases, oligonucleotide modifications which enhance target binding affinity are also, independently, able to enhance nuclease resistance. Oligonucleotides which contain at least one phosphorothioate modification are presently more preferred.

The oligonucleotides in accordance with this invention preferably are from about 5 to about 50 nucleotides in length. In the context of this invention it is understood that this encompasses non-naturally occurring oligomers as hereinbefore described, having 5 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as those available from Glen Research, Sterling VA, to synthe-size modified oligonucleotides such as cholesterol-modified oligonucleotides.

Methods of modulating the activity of HCV virus are provided, in which the virus, or cells, tissues or bodily fluid suspected of containing the virus, is contacted with an oligonucleotide of the invention. In the context of this invention, to "contact" means to add the oligonucleotide to a preparation of the virus, or vice versa, or to add the oligonucleotide to a preparation or isolate of cells, tissues or bodily fluid, or vice versa, or to add the oligonucleotide to virus, cells tissues or bodily fluid in situ, i.e., in an animal, especially a human.

The oligonucleotides of this invention can be used in diagnostics, therapeutics and as research reagents and kits. Since the oligonucleotides of this invention hybridize to RNA from HCV, sandwich and other assays can easily be constructed to exploit this fact. Provision of means for detecting hybridization of oligonucleotide with HCV or HCV RNA present in a sample suspected of containing it can routinely be accomplished. Such provision may include enzyme conjugation, radiolabelling or any other suitable detection systems. Kits for detecting the presence or absence of HCV may also be prepared. The specific ability of the oligonucleotides of the invention to inhibit HCV RNA function can also be exploited in the detection and diagnosis of HCV, HCV infection and HCV-associated diseases. As described in the examples of the present application, the decrease in HCV RNA or protein levels as a result of oligonucleotide inhibition of HCV RNA function can be routinely detected, for example by RT-PCR, Northern blot, Western blot or ELISA.

For prophylactics and therapeutics, methods of preventing HCV-associated disease and of treating HCV infection and HCV-associated disease are provided. The formulation of therapeutic compositions and their subsequent administration is believed to be within the skill in the art. Oligonucleotides may be formulated in a pharmaceutical composition, which may include carriers, thickeners, diluents, buffers, preservatives, surface active agents, liposomes or lipid formulations and the like in addition to the oligonucleotide. Pharmaceutical compositions may also include one or more active ingredients such as antimicrobial agents, anti-inflammatory agents, anesthetics, and the like. Formulations for parenteral administration may include sterile aqueous solutions which may also contain buffers, liposomes, diluents and other suitable additives.

The pharmaceutical composition may be administered in a number of ways depending on whether local or systemic treatment is desired, and on the area to be treated. Administration may be topical (including ophthalmic, vaginal, rectal, intranasal), oral, by inhalation, or parenteral, for example by intravenous drip or intravenous, subcutaneous, intraperitoneal or intramuscular injection.

Dosing is dependent on severity and responsiveness of the condition to be treated, with course of treatment lasting from several days to several months or until a reduction in viral titer (routinely measured by Western blot, ELISA, RT-PCR, or RNA (Northern) blot, for example) is effected or a diminution of disease state is achieved. Optimal dosing schedules are easily calculated from measurements of drug accumulation in the body. Persons of ordinary skill can easily determine optimum dosages, dosing methodologies and repetition rates. Therapeutically or prophylactically effective amounts (dosages) may vary depending on the relative potency of individual compositions, and can generally be routinely calculated based on molecular weight and $EC_{50}$s in in vitro and/or animal studies. For example, given the molecular weight of drug compound (derived from oligonucleotide sequence and chemical structure) and an experimentally derived effective dose such as an $IC_{50}$, for example, a dose in mg/kg is routinely calculated. In general, dosage is from 0.001 µg to 100 g and may be administered once or several times daily, weekly, monthly or yearly, or even every 2 to 20 years.

Pharmacokinetics of Antisense Oligonucleotides

Because the primary pathology associated with HCV infection occurs in the liver of infected individuals, the ability of a potential anti-HCV compound to achieve significant concentrations in the liver is advantageous. Pharmacokinetic profiles for a number of oligonucleotides, primarily phosphorothioate oligonucleotides, have been determined. Phosphorothioate oligonucleotides have been shown to have very similar pharmacokinetics and tissue distribution, regardless of sequence. This is characterized in plasma by a rapid distribution phase (approximately 30 minutes) and a prolonged elimination phase (approximately 40 hours). Phosphorothioates are found to be broadly distributed to peripheral tissues (i.e., excepting the brain, which is reachable directly, e.g., by intraventricular drug administration), with the highest concentrations found in liver, renal cortex and bone marrow. There is good accumulation of intact compound in most tissues, particularly liver, kidney and bone marrow, with very extended compound half-life in tissues. A preliminary study in mice using a 27-base phosphorothioate oligonucleotide indicated that greater than 40% of bioavailable compound resulting from a single, intravenous dose can be isolated from the liver at 12 hours after injection. Similar distribution profiles are found whether the oligonucleotide is administered intravenously or subcutaneously. Furthermore, the pharmacokinetic and tissue distribution profiles are very consistent among animal species, including rodents, monkeys and humans.

Preferred Embodiments of the Invention

It has been found that antisense oligonucleotides designed to target viruses can be effective in diminishing viral infection.

In accordance with this invention, persons of ordinary skill in the art will understand that messenger RNA includes not only the sequence information to encode a protein using the three letter genetic code, but also associated ribonucleotides which form regions known to such persons as the 5'-untranslated region, the 3'-untranslated region, and the 5' cap region, as well as ribonucleotides which form various secondary structures. Thus, oligonucleotides may be formulated in accordance with this invention which are targeted wholly or in part to these associated ribonucleotides as well as to the coding ribonucleotides. In preferred embodiments, the oligonucleotide is specifically hybridizable with the HCV 5' end hairpin loop, 5' end 6-base-pair repeats, ORF 3 translation initiation codon, (all of which are contained within the 5' UTR) polyprotein translation initiation codon, core protein coding region (both of which are contained within the coding region), R2 region, 3' hairpin loop or 3' end palindrome region (all of which are contained within the 3'-untranslated region). It is preferred that oligonucleotides have between about 5 and about 50 nucleotide units. The oligonucleotide may be modified to increase nuclease resistance and to increase its efficacy.

It is to be-expected that differences in the RNA of HCV from different strains and from different types within a strain exist. It is believed that the regions of the various HCV strains serve essentially the same function for the respective strains and that interference with homologous or analogous RNA regions will afford similar results in the various strains. This is believed to be so even though differences in the nucleotide sequences among the strains exist.

Accordingly, nucleotide sequences set forth in the present specification will be understood to be representational for the particular strain being described. Homologous or analogous sequences for different strains of HCV are specifically contemplated as being within the scope of this invention. In preferred embodiments of the present invention, antisense oligonucleotides are targeted to the 5' untranslated region, core protein translation initiation codon region, core protein coding region, ORF 3 translation initiation codon and 3'-untranslated region of HCV RNA.

In preferred embodiments, the antisense oligonucleotides are complementary to and hybridizable with at least a portion of the loop B region or loop C region of the 5'-untranslated region of the HCV RNA. Examples of such preferred antisense oligonucleotides comprise, for example, SEQ ID NO: 33, SEQ ID NO: 41, SEQ ID NO: 20, SEQ ID NO: 38, SEQ ID NO: 39, SEQ ID NO: 40, SEQ ID NO: 42, SEQ ID NO: 44, SEQ ID NO: 45 and SEQ ID NO: 48. Also preferred are oligonucleotides targeted to nucleotides 104–129 of the HCV RNA genome; this is a preferred target region.

In a preferred embodiment, the antisense oligonucleotides are complementary to and hybridizable with at least a portion of the loop F region of the 5'-end untranslated region of an HCV RNA. A more preferred antisense oligonucleotide comprises SEQ ID NO: 62. Other more preferred antisense oligonucleotides comprise SEQ ID NOs: 63, 99, 100, 101, 102, 103, 104, 105, 106 and 107 and oligonucleotides targeted to nucleotides 254–289 of HCV RNA. This target region is highly preferred.

In a preferred embodiment, the antisense oligonucleotides are hybridizable with the nucleotide sequence GCCUCCAGGACCCC (SEQ ID NO: 97) which is present at the 5'-untranslated region of the HCV genome, or with a nucleotide sequence which is highly homologous to said nucleotide sequence, differing from said nucleotide sequence merely in one or two base units. Such oligonucleotides are at least 14 nucleotides long, preferably 14 to 26 nucleotides long. Thus, the preferred oligonucleotides contain a sequence complementary to the target nucleotide sequence GCCUCCAGGACCCC.

More preferable oligonucleotides have a nucleotide sequence which is hybridizable to said nucleotide sequence and further contains a nucleotide sequence complementary to the following target nucleotide sequence: CGUGCAGCCUCCAGGACCCCCCCUCC (SEQ ID NO: 98; region in bold is equivalent to SEQ ID NO: 97 above) found at nucleotides 104–129 of the 5' end untranslated region of HCV RNA, or to a continuous nucleotide sequence of about 20 nucleotides long within this 26 mer nucleotide sequence.

In other preferred embodiments, the oligonucleotides are hybridizable with at least a portion of the polyprotein translation initiation codon or with at least a portion of the core protein coding region. In a more preferred embodiment, the oligonucleotides contain an antisense nucleotide sequence GGAT which is specifically hybridizable with a nucleotide sequence AUCC of the genome of HCV, which is present at nucleotides 352 to 355 in the core protein coding region near the polyprotein translation initiation codon. Examples of such highly preferred oligonucleotides hybridizable with at least a portion of the polyprotein translation initiation codon are SEQ ID NO: 81, SEQ ID NO: 82, SEQ ID NO: 72, SEQ ID NO: 76, SEQ ID NO: 77, SEQ ID NO: 78, SEQ ID NO: 79, SEQ ID NO: 80 and SEQ ID NO: 73. Examples of the highly preferred oligonucleotides hybridizable with at least a portion of the core protein coding region of an HCV RNA are SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91 and SEQ ID NO: 93. Suitable examples of the oligonucleotides hybridizable with a nucleotide sequence of the nucleotide number 352 to 355 (AUCC) of HCV DNA are SEQ ID NO: 76, SEQ ID NO: 77, SEQ ID NO: 78, SEQ ID NO: 79, SEQ ID NO: 80, SEQ ID NO: 84, SEQ ID NO: 85, SEQ ID NO: 86 and SEQ ID NO: 87. Oligonucleotides hybridizable with the regions of the coding region from nucleotide 344 to nucleotide 380 are highly preferred, and this is a highly preferred target region. Oligonucleotides targeted to this region which contain at least one 2' fluoro modification are most preferred, particularly those which contain such a modification on every nucleotide. Highly preferred examples of such oligonucleotides are those targeted to HCV sequences beginning at nucleotides 344, 345, 347 and 355.

In vitro Evaluation of HCV Antisense Oligonucleotides

HCV replication in cell culture has not yet been achieved. Consequently, in vitro translation assays are used to evaluate antisense oligonucleotides for anti-HCV activity. One such in vitro translation assay was used to evaluate oligonucleotide compounds for the ability to inhibit synthesis of HCV 5' UTR-core-env transcript in a rabbit reticulocyte assay.

Cell-based assays are also used for evaluation of oligonucleotides for anti-HCV activity. In one such assay, effects of oligonucleotides on HCV RNA function are evaluated by measuring RNA and/or HCV core protein levels in transformed hepatocytes expressing the 5' end of the HCV genome. Recombinant HCV/vaccinia virus assays can also be used, such as those described in the examples of the present application. Luciferase assays can also be used, for example, as described in the examples of the present application, in which recombinant vaccinia virus containing HCV sequences fused to luciferase sequences are used. Quantitation of luciferase with a luminometer is a simple way of measuring HCV core protein expression and its inhibition by antisense compounds. This can be done in cultured hepatocytes or in tissue samples, such as liver biopsies, from treated animals.

Animal Models for HCV

A recombinant vaccinia/HCV/luciferase virus expression assay is presently being evaluated in mice. Mice are inoculated intraperitoneally or intravenously with recombinant vaccinia virus (either expressing HCV/luciferase or luciferase alone for a control). Liver, spleen and kidney are harvested two or four days later and luciferase activity in the tissue is assayed by luminometry.

A chimpanzee model for HCV is presently the only available animal model for chronic HCV infection because chimps are the only animal, other than man, known to become chronically infected with the human HCV virus. Chimps are treated with oligonucleotide, either by continuous I.V. infusion or injection and bled periodically over succeeding days and weeks to determine the effect of oligonucleotide on viral RNA titer, which is routinely measured by RT-PCR or Northern blot analysis in accordance with well-known methodologies in the art.

The sequences of a number of oligonucleotides targeted to HCV are shown in Table 1. A number of similar oligonucleotides can easily be designed and made by one skilled in the art, based on the teachings of the present invention.

TABLE 1

RNA SEQUENCE TARGETS AND ANTISENSE
OLIGONUCLEOTIDES FOR HCV

[Sequences are from HCV-1 (US) and HCV-J (Japan)]

| SEQ ID NO: | Antisense oligo sequence: | Target description: | Target strand: |
|---|---|---|---|
| 1 | 5'-ATG GTG GAG TGT CGC CCC GTC-3' | 5' end hairpin | + |
| 2 | 5'-GGA GTG ATC TAT GGT GGA GTG-3' | 5' end 6-bp repeat | + |

TABLE 1-continued

RNA SEQUENCE TARGETS AND ANTISENSE OLIGONUCLEOTIDES FOR HCV

[Sequences are from HCV-1 (US) and HCV-J (Japan)]

| SEQ ID NO: | Antisense oligo sequence: | Target description: | Target strand: |
|---|---|---|---|
| 3 | 5'-GAT TCG TGC TCA TGG TGC ACG-3' | Polyprotein AUG | + |
| 4 | 5'-TCC AGG CAT TGA GCG GGT TGA-3' | ORF 3 AUG | + |
| 5 | 5'-TGG CCT GGA GTG TTT ATC TCC-3' | 3'-untranslated | + |
| 6 | 5'-GGG GTA GGC ATC TAC CTG CTC-3' | 3' palindrome | - |
| 7 | 5'-CGC CCC CAT CAG GGG GCT GGC-3' | 5' end hairpin | + |
| 8 | 5'-TTC ATG GTG GAG TGT CGC CCC-3' | 5' end hairpin | + |
| 9 | 5'-GTT CCT CAC AGG GGA GTG ATT-3' | 5' untranslated | + |
| 10 | 5'-TAC TAA CGC CAT GGC TAG ACG-3' | 5' untranslated | + |
| 11 | 5'-CTA TGG CTC TCC CGG GAG GGG-3' | 5' untranslated | + |
| 12 | 5'-CCA CTA TGG CTC TCC CGG GAG-3' | 5' untranslated | + |
| 13 | 5'-CGG TGT ACT CAC CGG TTC CGC-3' | 5' untranslated | + |
| 14 | 5'-CTG GCA ATT CCG GTG TAC TCA-3' | 5' untranslated | + |
| 15 | 5'-GGG GCA CGC CCA AAT CTC CAG-3' | 5' untranslated | + |
| 16 | 5'-CCT TTC GCG ACC CAA CAC TAC-3' | 5' untranslated | + |
| 17 | 5'-CCC TAT CAG GCA GTA CCA CAA-3' | 5' untranslated | + |
| 18 | 5'-CTC CCG GGG CAC TCG CAA GCA-3' | 5' untranslated | + |
| 19 | 5'-CAT GGT GCA CGG TCT ACG AGA-3' | Polyprotein AUG | + |
| 20 | 5'-GAT TCG TGC TCA TGG TGC ACG-3' | Polyprotein AUG | + |
| 21 | 5'-TTT AGG ATT CGT GCT CAT GGT-3' | Polyprotein AUG | + |
| 22 | 5'-GAG TGG TTA GCC CAA TCT TCA-3' | 3' untranslated | + |
| 23 | 5'-TAT TGG CCT GGA GTG GTT AGC-3' | R2 | + |
| 24 | 5'-AGG GAA TGG CCT ATT GGC CTG-3' | R2/3' hairpin | + |

The following specific examples are provided for illustrative purposes only and are not intended to limit the invention.

EXAMPLES

Example 1

Oligonucleotide Synthesis

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2 -benzodithiole-3-one 1,1-dioxide in acetonitrile for the stepwise thiation of the phosphite linkages. The thiation cycle wait step was increased to 68 seconds and was followed by the capping step.

2'-O-methyl oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

2'-O-propyl oligonucleotides were prepared from 2'-deoxy-2'-O-propyl ribosides of nucleic acid bases A, G, U(T), and C which were prepared by modifications of literature procedures described by B. S. Sproat et al., *Nucleic Acids Research* 1990, 18, 41–49 and H. Inoue et al., *Nucleic Acids Research* 1987, 15, 6131–6148.

2'-fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and U.S. patent application Ser. No. 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

2'-methoxyethoxy modified phosphoramidites were synthesized according to Martin et al., 1995, Helv. Chim. Acta, 78:486–504.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0.

Example 2

Screening of Oligonucleotides by in vitro Translation Assay

Preparation of HCV RNA to Be Used for in vitro Translation

An RNA having a sequence homologous to nucleotides 1–686 of HCV was prepared in the following manner, wherein the stop codon (TGA) was added to the 3'-terminus.

(1) Preparation of Template HCV-cDNA for Polymerase Chain Reaction (PCR)

Based on a cDNA nucleotide sequence prepared by the present inventors by cloning from serum of a Japanese patient of Hepatitis C, a 686-nucleotide cDNA was cloned, which included the full length 5'-untranslated region of HCV (342 nucleotide sequence) and an adjacent core region (145 nucleotide sequence).

(2) Preparation of Primers for PCR

A 41-nucleotide sense primer was prepared which contained an EcoRI cleavage site, a T7 promoter and 14 bases (nucleotide number 1–14) of HCV nucleotide sequence in this order from the 5'-terminus. A 27-nucleotide antisense primer containing an EcoRI cleavage site, 3 bases which are complementary to the stop codon (TGA) and 15 bases which are complementary to the region of the base number 672–686 of HCV nucleotide sequence (in this order from the 5'-terminus) was also prepared, by a solid phase phosphoramidite method with Cyclone Plus DNA Synthesizer (manufactured by MilliGen/Biosearch).

(3) Preparation of Template DNA for Synthesis of RNA by PCR

PCR was performed (20 cycles) using the cDNA and primers prepared in (1) and (2). The PCR was performed under denaturing conditions: 94° C. for one minute, annealing: 55° C. for 2 minutes, polymerase reaction: 72° C. for 2 minutes. The resulting DNA fragment was treated with EcoRI and inserted into EcoRI site of pUC19, and *E. coli* JM 109 strain was transformed with the resultant recombinant plasmid by a conventional method. Plasmids from transformed bacterial colonies were sequenced to confirm the insertion of 686 nucleotides derived from HCV. One such plasmid was designated "pUIA1".

(4) Preparation of RNA Having Nucleotides 1–686 of HCV

The EcoRI insert was taken out of the pUIA1by treating it with EcoRI, and used as a template to synthesize a 698-nucleotide RNA (using MEGAscript in vitro Transcription Kit, Ambion), consisting of nucleotides 1–686 of HCV, a stop codon (UGA) and an EcoRI cleavage site (in this order from the 5'-terminus). This fragment was designated "R-IA-1". The nucleotide sequence of the 686 bases derived from HCV in said R-IA-1 is shown in the accompanying FIG. 1.

Synthesis of HCV Core Protein in Cell-free Translation System

An HCV core protein was translated from R-IA-1 in a cell-free rabbit reticulocyte lysate system. The expression of HCV core protein was confirmed by ELISA as follows.

(1) Construction of ELISA System for Quantitatively Determining HCV Core Protein The core region of HCV was directly expressed in *E. coli* by a conventional method. A mouse was immunized with the expressed protein thus obtained, and two kinds of monoclonal antibodies, RJC4-1 (IgM type) and RJC4-2 (IgG type) were obtained therefrom by conventional methods. Monoclonal antibody RJC4-1 was diluted to 50 μg/ml with 10 mM PBS, and 50 μl of diluted RJC4-1 was added to each well of a MaxiSorp F8 plate (Nunc). After incubation at 4° C. overnight, the remaining antibody solution was removed by suction from the well. The wells were blocked at 4° C. overnight with 150 μl of PBS containing 1% calf serum albumin and then washed. The core protein, prepared using rabbit reticulocyte extract, was diluted to an appropriate concentration with PBS containing 1% calf serum albumin, and 50 μl of the diluted core protein was added to each well. The mixture was incubated at room temperature for 2 hours and then washed. Thereafter, the antibody RJC4-2 (50 μl) bound with a horseradish peroxidase was added to each well, and the mixture was incubated at 37° C. for one hour and then washed. Lastly, an aqueous solution of 3,3',5,5'-tetramethylbenzidine (50 μl) was added to each well, and the mixture was incubated at room temperature for 15 minutes, then the reaction was stopped with 1 N sulfuric acid. The absorbance (450 nm) of the reaction mixture was measured. As a result, it was found that the HCV core protein could be determined quantitatively by ELISA.

(2) Expression of HCV Core Protein with a Rabbit Reticulocyte Lysate 20 pmol of R-IA-1 in 10 μl TE (10 mM Tris, 1 mM EDTA, pH 7.4) was mixed with an aqueous solution of methionine (2 μl) to give a final methionine concentration of 10 μM. A negative control solution of 10 μl TE without RNA was similarly mixed with 2 μl methionine. To each mixture (12 μl) was added 20 μl of rabbit reticulocyte lysate (In Vitro Translation Kit; Stratagene, La Jolla, Calif.), and the mixture was incubated at 30° C. for 2 hours. The reaction mixture was diluted and then the core protein was quantitated by ELISA. It was thereby confirmed that the HCV core protein was synthesized in the positive control (with RNA), but no HCV core protein was found in the negative control (without RNA).

Search of Target Region of Antisense Compounds

Oligonucleotides complementary to the 5'-untranslated region of HCV RNA were screened as follows for ability to inhibit the translation of HCV core protein in vitro.

(1) Preparation of Synthetic Antisense DNA Oligonucleotides

Antisense oligonucleotides were prepared by a solid phase phosphoamidite method as in Example 1 (for oligonucleotides designated "IA-") or using a Cyclone Plus DNA Synthesizer (manufactured by MilliGen/Biosearch) (for oligonucleotides designated "CAS-"). The product thus obtained was treated with phenol and subjected to ethanol precipitation. The precipitate was dissolved in 10 mM Tris-HCl (pH 8.0)-1 mM EDTA solution for use in the subsequent procedure.

The antisense oligonucleotides were each 20 nucleotides in length. The "CAS-" or "IA-" number used to denominate each sequence refers to the number of the 5'-most nucleotide of the complementary HCV RNA target sequence shown in the accompanying FIG. 1.

(2) Evaluation of Inhibitory Activity of the Antisense Oligonucleotides

R-IA-1 (20 pmol) and an antisense DNA to be tested (100 pmol) were mixed in TE (final volume, 10 μl), and the mixture was incubated at room temperature for 10 minutes. To the solution was added 10 mM aqueous methionine solution (2 μl), and 20 μl of rabbit reticulocyte lysate (In Vitro Translation Kit; Stratagene, La Jolla Calif.). The mixture was incubated at 30° C. for 2 hours, after which the core protein produced in the reaction mixture was quantitatively determined by ELISA. Results were expressed as percent inhibition of core protein expression, compared to control (no antisense oligonucleotide).

(3) Screening for Target Regions Effective for Inhibition of the Growth of HCV

Antisense oligonucleotides (P=O) were synthesized which are complementary to target sequences located at 10-nucleotide intervals from nucleotide 1 to 339 in the HCV RNA 5'-untranslated region. The sequences of these oligonucleotides, CAS-1 through CAS-320, are shown in Table 2.

TABLE 2

Antisense oligonucleotides to HCV

| Oligo | Sequence | SEQ ID NO: |
|---|---|---|
| CAS-1 | GCC CCG AAT CGG GGG CTG GC | 26 |
| CAS-10 | TGG AGT GTC GCC CCC AAT CG | 27 |
| CAS-20 | TGA TCT ATG GTG GAG TGT CG | 28 |
| CAS-30 | CAC AGG GGA GTG ATC TAT GG | 29 |
| CAS-40 | AGT AGT TCC TCA CAG GGG AG | 30 |
| CAS-50 | GCG TGA AGA CAG TAG TTC CT | 31 |
| CAS-60 | GAC GCT TTC TGC GTG AAG AC | 32 |
| CAS-70 | GCC ATG GCT AGA CGC TTT CT | 33 |
| CAS-80 | TCA TAC TAA CGC CAT GGC TA | 34 |
| CAS-90 | TGC ACG ACA CTC ATA CTA AC | 35 |
| CAS-100 | TCC TGG AGG CTG CAC GAC AC | 36 |
| CAS-101 | GTC CTG GAG GCT GCA CGA CA | 20 |
| CAS-102 | GGT CCT GGA GGC TGC ACG AC | 37 |
| CAS-104 | GGG GTC CTG GAG GCT GCA CG | 38 |
| CAS-106 | GGG GGG TCC TGG AGG CTG CA | 39 |
| CAS-108 | AGG GGG GGT CCT GGA GGC TG | 40 |
| CAS-110 | GGA GGG GGG GTC CTG GAG GC | 41 |
| CAS-110-I-119 | GGA GGG GGG GIC CTG GAG GC | 42 |
| CAS-110-G-119 | GGA GGG GGG GGC CTG GAG GC | 43 |
| CAS-112 | CGG GAG GGG GGG TCC TGG AG | 44 |
| CAS-114 | CCC GGG AGG GGG GGT CCT GG | 45 |
| CAS-116 | CTC CCG GGA GGG GGG GTC CT | 46 |
| CAS-118 | CTC TCC CGG GAG GGG GGG TC | 47 |
| CAS-120 | GGC TCT CCC GGG AGG GGG GG | 48 |
| CAS-130 | AGA CCA CTA TGG CTC TCC CG | 49 |
| CAS-140 | CCG GTT CCG CAG ACC ACT AT | 50 |
| CAS-150 | GGT GTA CTC ACC GGT TCC GC | 51 |
| CAS-160 | TGG CAA TTC CGG TGT ACT CA | 52 |
| CAS-170 | CCG GTC GTC CTG GCA ATT CC | 53 |
| CAS-180 | AAG AAA GGA CCC GGT CGT CC | 54 |
| CAS-190 | GGG TTG ATC CAA GAA AGG AC | 55 |
| CAS-200 | GGC ATT GAG CGG GTT GAT CC | 56 |

TABLE 2-continued

Antisense oligonucleotides to HCV

| Oligo | Sequence | SEQ ID NO: |
|---|---|---|
| CAS-210 | CAA ATC TCC AGG CAT TGA GC | 57 |
| CAS-220 | GGG GCA CGC CCA AAT CTC CA | 58 |
| CAS-230 | CAG TCT CGC GGG GGC ACG CC | 59 |
| CAS-240 | ACT CGG CTA GCA GTC TCG CG | 60 |
| CAS-250 | ACC CAA CAC TAC TCG GCT AG | 61 |
| CAS-260 | GCC TTT CGC GAC CCA ACA CT | 62 |
| CAS-270 | GTA CCA CAA GGC CTT TCG CG | 63 |
| CAS-280 | CTA TCA GGC AGT ACC ACA AG | 64 |
| CAS-290 | CGC AAG CAC CCT ATC AGG CA | 65 |
| CAS-300 | CCG GGG CAC TCG CAA GCA CC | 66 |
| CAS-310 | ACG AGA CCT CCC GGG GCA CT | 67 |
| CAS-320 | TGC ACG GTC TAC GAG ACC TC | 68 |

The inhibitory activity of these antisense oligonucleotides was tested using the HCV in vitro core protein translation assay. Oligonucleotides CAS-70, which is complementary to a portion of loop B, and CAS-110, which is complementary to a portion of loop C, were found to cause greater than 90% inhibition of core protein translation and are most preferred. These results are shown in FIG. 2.

(4) Analysis of the Nucleotide 100–140 Region in More Detail

Additional oligonucleotides which are complementary to the region from nucleotide 100 to 140 of HCV RNA, which includes the loop C region, were synthesized and tested in the in vitro translation assay. These oligonucleotides are shown in Table 2. As shown in FIG. 2, oligonucleotides CAS-101, CAS-104, CAS-106, CAS-108 and CAS-114 were found to inhibit HCV core protein translation in vitro by 70% or more and are preferred. Oligonucleotides CAS-104, CAS-106 and CAS-108 showed greater than 90% inhibition and are more preferred. The antisense oligonucleotides complementary to the 26-base region of HCV RNA from nucleotides 104 to 129 showed strong inhibitory activity against the translation of the HCV-RNA in comparison with the antisense oligonucleotides complementary to other regions of 5'-untranslated region. Oligonucleotides hybridizable with this region are therefore preferred.

Additional oligonucleotides complementary to the region from nucleotide 62 to 78 in the loop B region of the HCV RNA were also tested and, of these, CAS-70 was found to be the most potent inhibitor of HCV core protein translation and is most preferred.

(5) Evaluation of Antisense Oligonucleotides Wherein the Base Number 119 Was Replaced by Inosine Because the nucleotide at position 119 in the loop C region has a high variation rate among HCV strains, various antisense oligonucleotides were prepared wherein the adenosine at this position was substituted by the "universal base" inosine in order to evaluate whether the substituted oligonucleotides would be effective for the inhibition of various virus strains.

An analog of CAS-110 was prepared in which the thymidine corresponding to adenosine at nucleotide number 119 was replaced by inosine to give CAS-110-I-119. As a reference, the sequence CAS-110-G-119 was also prepared, in which said thymidine was replaced by guanosine so as to make an artificial mismatch. These sequences are shown in Table 2. The inhibitory activity of these oligonucleotides was evaluated in the in vitro translation assay. As a result, CAS-110-I-119 showed an inhibitory activity of more than 70% similar to CAS-110, but CAS-110-G-119 showed much lower activity. CAS-110-I-119 is therefore preferred. It is likely from the result that the compound obtained by replacing thymidine with inosine would be effective against other virus strains in which adenosine at position 119 is replaced by another nucleotide.

(6) Evaluation of 2'-O-methyl Antisense Oligonucleotides

The binding affinity of antisense oligonucleotides for their target sequence is enhanced by methoxylation of the 2'-position of the sugar moiety in the antisense oligonucleotide. 2'-O-methylated oligonucleotides were prepared having the sequences shown in Table 2 (other than the two substituted by inosine) and their inhibitory activity was evaluated in the in vitro translation assay. The CAS-260 sequence, hybridizing to the loop F region, appeared to be significantly more active when 2'-O-methylated, showing greater than 75% inhibition. This compound is therefore preferred. Activities of some of the tested oligonucleotides are shown in FIG. 3.

Example 3

Evaluation of Inhibitory Activity of Antisense Oligonucleotides Which are Targeted to the Polyprotein Translation Initiation Codon Region and Adjacent Core Protein Coding Region (1) In order to evaluate the inhibitory activity of antisense oligonucleotides which are complementary to the region including the translation initiation codon (nucleotide number 342-344) of HCV-RNA and the adjacent core protein coding region, a series of 20 mer antisense oligonucleotides were prepared which are complementary to the region from nucleotide 320 to nucleotide 379. Of these, CAS-324 through CAS-344 contain all or part of the sequence CAT which is complementary to the AUG initiation codon itself. The nucleotide sequence of these antisense oligonucleotides are shown in the accompanying Table 3.

TABLE 3

Antisense oligonucleotides to HCV

| Oligo | Sequence | % inhibition | SEQ ID NO: |
|---|---|---|---|
| CAS-320 | TGC ACG GTC TAC GAG ACC TC | 3 | 68 |
| CAS-322 | GGT GCA CGG TCT ACG AGA CC | 5 | 69 |
| CAS-324 | ATG GTG CAC GGT CTA CGA GA | 31 | 70 |
| CAS-326 | TCA TGG TGC ACG GTC TAC GA | 39 | 71 |
| CAS-328 | GCT CAT GGT GCA CGG TCT AC | 71 | 72 |
| CAS-330 | GTG CTC ATG GTG CAC GGT CT | 38 | 73 |
| CAS-332 | TCG TGC TCA TGG TGC ACG GT | 5 | 74 |
| CAS-334 | ATT CGT GCT CAT GGT GCA CG | 39 | 75 |
| CAS-336 | GGA TTC GTG CTC ATG GTG CA | 98 | 76 |
| CAS-338 | TAG GAT TCG TGC TCA TGG TG | 99 | 77 |
| CAS-340 | TTT AGG ATT CGT GCT CAT GG | 97 | 78 |
| CAS-342 | GGT TTA GGA TTC GTG CTC AT | 96 | 79 |
| CAS-344 | GAG GTT TAG GAT TCG TGC TC | 99 | 80 |
| CAS-344-i1 | GAG GTT TAG GAT TIG TGC TC | 95 | 81 |
| CAS-344-i3 | GIG GTT TIG GAT TIG TGC TC | 90 | 82 |
| CAS-344-i5 | GIG GTT TIG GAI IIG TGC TC | 51 | 83 |
| CAS-346 | TTG AGG TTT AGG ATT CGT GC | 98 | 84 |
| CAS-348 | CTT TGA GGT TTA GGA TTC GT | 98 | 85 |
| CAS-350 | TTC TTT GAG GTT TAG GAT TC | 99 | 86 |
| CAS-352 | TTT TCT TTG AGG TTT AGG AT | 99 | 87 |
| CAS-354 | GTT TTT CTT TGA GGT TTA GG | 91 | 88 |
| CAS-356 | TGG TTT TTC TTT GAG GTT TA | 86 | 89 |
| CAS-358 | TTT GGT TTT TCT TTG AGG TT | 83 | 90 |
| CAS-360 | CGT TTG GTT TTT CTT TGA GG | 81 | 91 |

The inhibitory activity of these 21 antisense oligonucleotides was evaluated in the in vitro translation assay. As shown in Table 3, antisense oligonucleotides CAS-328, CAS-336, CAS-338, CAS-340, CAS-342, CAS-344, CAS-346, CAS-348, CAS-350, CAS-352, CAS-354, CAS-356, CAS-358 and CAS-360 showed an inhibitory activity of greater than 70%, and are preferred. Of these, CAS-336, CAS-338, CAS-340, CAS-342, CAS-344, CAS-346, CAS-348, CAS-350 and CAS-352 showed an extremely high inhibitory activity of over 95% and are most preferred.

The HCV target sequence regions complementary to the above 9 most active antisense oligonucleotides have in common the four nucleotides from number 352 to 355 in the core protein coding region near the polyprotein translation initiation codon. Thus, it is preferred to target these four nucleotides in order to inhibit the translation. Accordingly, oligonucleotides comprising the sequence GGAT are preferred embodiments of the invention.

(2) Evaluation of Antisense Oligonucleotides in Which the Nucleotides Known to Be Variable Among Strains Were Replaced by Inosine It is known that in the nucleotide sequences in the core protein coding region near the translation initiation codon, variation of bases among strains occasionally occurs at nucleotides 350, 351, 352, 356 and 362. Based on this knowledge, it was studied whether substitution of these bases by the "universal base" inosine would be effective for inhibition of various viruses.

An antisense DNA, designated CAS-344-i1, was prepared in which the base at base number 350 in CAS-344 was replaced by inosine. Likewise, an antisense DNA, designated CAS-344-i3, in which three bases at base numbers 350, 356 and 362 were substituted by inosine, and an antisense DNA, designated CAS-344-i5, in which five bases at base numbers 350, 351, 352, 356, and 362 were substituted by inosine, were prepared. The inhibitory activity of these antisense oligonucleotides was evaluated in the in vitro translation assay. As a result, the CAS-344-i1 and CAS-344-i3 showed high inhibitory activity. Therefore, antisense oligonucleotides of sequence CAS-344 which have three inosine substituents or less are preferred. Their inhibitory activities are shown in the accompanying Table 3.

Example 4

Evaluation of Antisense DNA in Transformed H8Ad17 Hepatocytes Which Express HCV Core Protein (1) Preparation of Phosphorothioate Oligonucleotides Because sequences CAS-110, CAS-260, CAS-344 and CAS-345 showed high inhibitory activity as phosphodiesters (P=O) in the in vitro translation assay, the corresponding phosphorothioate (P=S) oligonucleotides were prepared. These oligonucleotides are designated by adding "S" after the name of each parent oligonucleotide, e.g., "CAS-110S", "CAS-260S" and the like. As a negative control, an oligonucleotide having a random sequence was prepared.

(2) Preparation of Liver Cell Transformant

An expression plasmid containing a gene (1.3 kb) coding for 5' NCR-core-env region of HCV gene was prepared by conventional methods and transfected into a liver cell strain (H8Ad17) by lipofection according to standard methods. The desired liver cell transformant, which expressed HCV core protein, was obtained.

(3) Detection System for Core Protein Expression by the Liver Cell Transformant

The core protein expressed by the liver cell transformant was detected by ELISA method using an anti-HCV core-mouse monoclonal antibody as the solid phase antibody; an anti-HCV human polyclonal antibody as the primary antibody; and an HRP (horseradish peroxidase)-conjugated anti-human IgG-mouse monoclonal antibody as the secondary antibody. By using this detection system, the core protein expressed by the liver cell transformant was measured.

(4) Evaluation of Antisense Oligonucleotides

The liver cell transformant ($2.5 \times 10_5$ cells) were inoculated on 6-well plates. To each plate was added each of the above-obtained five antisense oligonucleotides (each at a concentration of 5 $\mu$M). After two days, the cells were harvested and counted. The cells were washed once and lysed, and the inhibitory activity was measured by ELISA.

The inhibitory activities of the five P=S antisense oligonucleotides were calculated, compared to control without antisense oligonucleotide. Phosphorothioate oligonucleotides CAS-110, CAS-260S, CAS-344S and CAS-345S showed inhibitory activities of approximately 30–45% in this in vivo assay. The cell toxicity of these antisense oligonucleotides was also evaluated. No cell toxicity was observed with these antisense oligonucleotides.

Example 5

Evaluation of Oligonucleotides in Modified in Vitro Core Protein Translation Assay The assay described in Example 2 was modified by construction of a T7-HCV-core-env fusion plasmid to eliminate the PCR amplification step. A T7 expression plasmid was constructed in which the HindIII to BamHI fragment containing HCV 5' noncoding region-core sequences was inserted into plasmid pGEM4Z. The resulting plasmid was linearized with BamHI and transcribed by T7 RNA polymerase. $^{35}$S-labeled in vitro translation products were analyzed by SDS-polyacrylamide gel electrophoresis. The optimal amount of T7 RNA transcript for use in translation assays was determined to be approximately 2.2 pmol RNA per reaction. In vitro translation of HCV RNAs of different sizes yielded products of the expected sizes.

Figure 4:
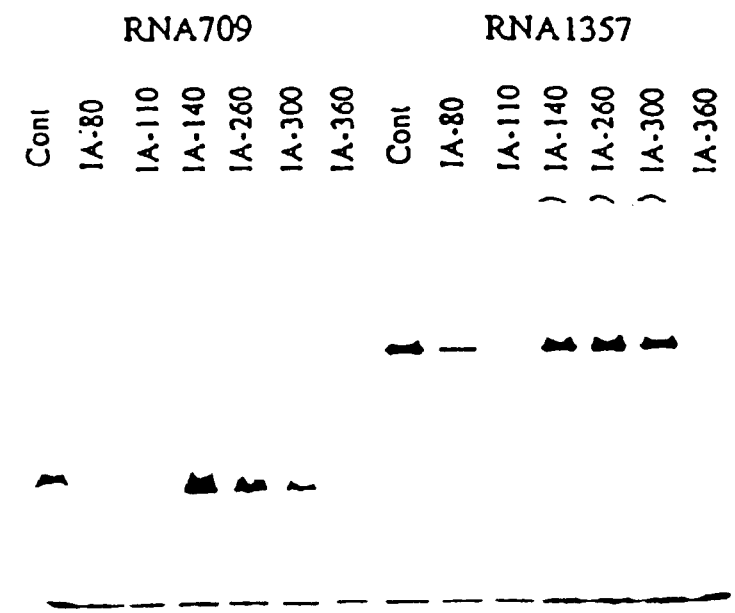
FIG. 4 is an autoradiograph showing inhibitory activities of oligonucleotides IA-80, IA-110, IA-140, IA-260, IA-300 and IA-360 against HCV core protein translation in vitro.

A number of phosphodiester (unmodified) oligonucleotides equivalent to those previously evaluated as described in Example 2 were evaluated in the modified in vitro translation assay. Oligonucleotides were resynthesized and were tested at a molar ration of 20:1. As shown in FIG. 4, oligonucleotides IA-80, IA-110, IA-140 and IA-360 (identical to the previously tested CAS-80, CAS-110, CAS-140 and CAS-360 sequences, respectively; the "IA" or "CAS" prefix indicates different lots synthesized at different facilities) showed activity in the modified assay comparable to that described in the previous examples. Oligonucleotides IA-140, IA-260 and IA-300 (identical to CAS-140, CAS-260 and CAS-300 sequences tested above) did not show good inhibition in this assay. IA-110 and IA-360 showed the best activity and the IA-80 sequence also was inhibitory in this assay.

Oligonucleotides with 2'-O-methyl Modifications

Figure 5:
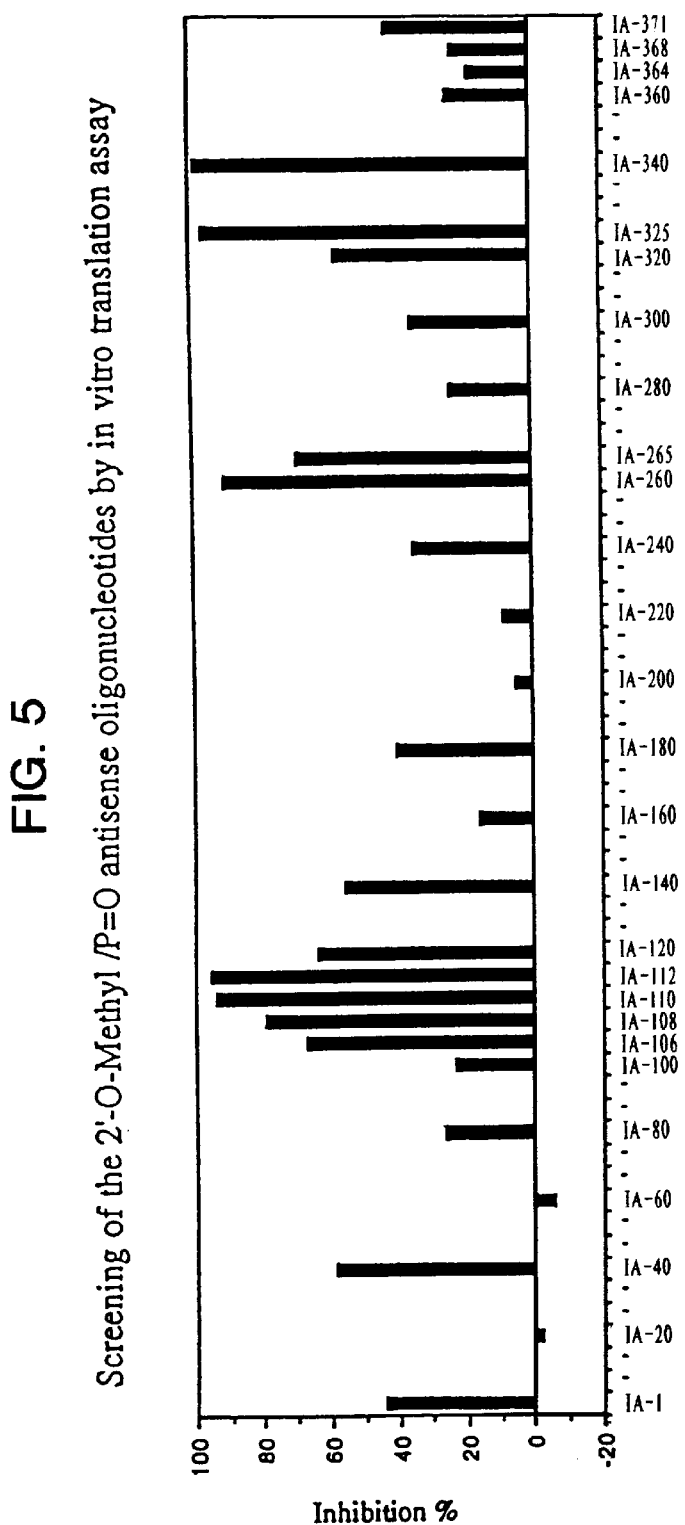
FIG. 5 is a bar graph showing inhibition of HCV core protein translation in the modified in vitro translation assay by oligonucleotides complementary to the region from nucleotide 1 to 371 of HCV RNA.

Oligonucleotide sequences previously tested as unmodified phosphodiester (P=O) compounds were synthesized as uniform 2'-O-methyl/P=O and tested in the modified in vitro translation assay. Results are shown in FIG. 5. Oligonucleotides IA-110, 112, 260, 325 and 340 showed inhibitory activity in agreement with previous results obtained with P=O oligonucleotides and are preferred. As found using the original assay system, oligonucleotide 260 was more active in 2'-O-methyl/P=O form than as unmodified phosphodiester.

Figure 6:
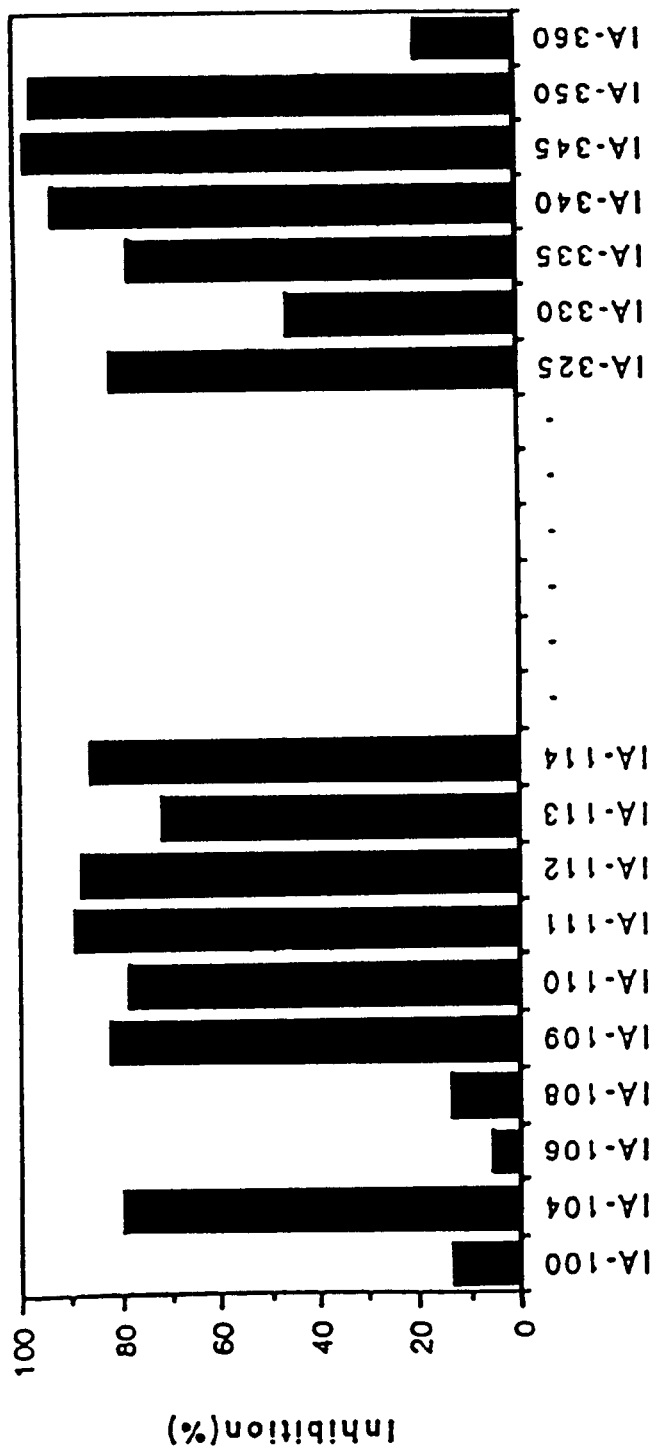
FIG. 6 is a bar graph showing inhibition of HCV translation by 2'-O-methyl/P=O antisense oligonucleotides around the loop C region and AUG codon/core protein coding region.

A panel of uniformly 2'-O-methylated phosphodiester oligonucleotides complementary to loop C sequences was evaluated using the modified in vitro translation assay to identify the oligonucleotide with the greatest inhibitory activity. A second panel of 2'O-methylated phosphodiester oligonucleotides complementary to the polyprotein initiation codon region was also tested. The results of these assays are shown in FIGS. 5 and 6. These results confirmed that antisense oligonucleotides complementary to the loop C region (around nucleotide 110), and polyprotein translation initiation codon region (around nucleotide 340) and adjacent core protein coding region show good inhibitory activity. Such oligonucleotides are preferred.

Evaluation of Phosphorothioate (P=S) Oligonucleotides

Figure 7:
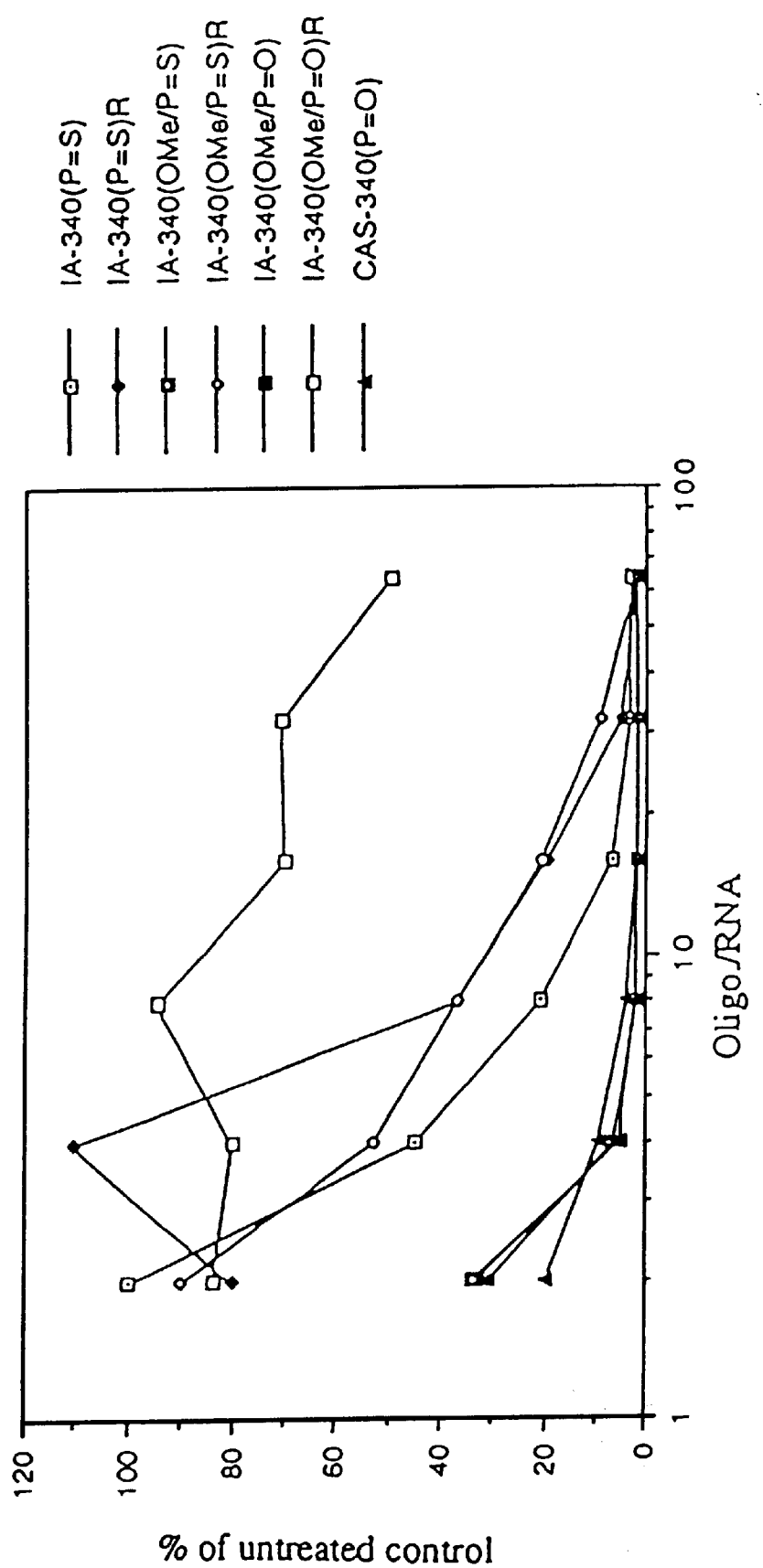
FIG. 7 is a line graph showing dose-dependent inhibition of HCV core protein translation by P=O, P=S, P=O/2'-O—Me and P=S/2'-O—Me versions of IA-340.

Phosphorothioate oligonucleotides IA-110 and IA-340 with 2'-O-methyl modifications throughout were evaluated using the modified in vitro translation assay. A comparison of inhibitory activities of phosphorothioate (P=S), phosphodiester (P=O), 2'-O-Me/P=S and 2'-O-Me/P=O oligonucleotides was performed. Randomized oligonucleotides (P=S R, 2'-O-Me/P=S R, 2'-O-Me/P=O R) were included in the assays to demonstrate specificity. All IA-110 oligonucleotides, regardless of modification, showed similar ability to inhibit HCV core protein translation. The randomized 110 sequence also showed comparable inhibitory activity, though randomization was not absolute because 13 of the 20 nucleotides in this sequence are G. Oligonucleotide 340 showed sequence-specific inhibition of HCV core protein translation since randomized 340 oligonucleotides showed considerably less inhibitory activity than antisense oligonucleotides. P=O, 2'-O-Me/P=O or 2'-OMe/P=S oligonucleotides with the 340 sequence showed similar near-total reduction in HCV core protein translation which was concentration-dependent, as shown in FIG. 7.

Figure 8:
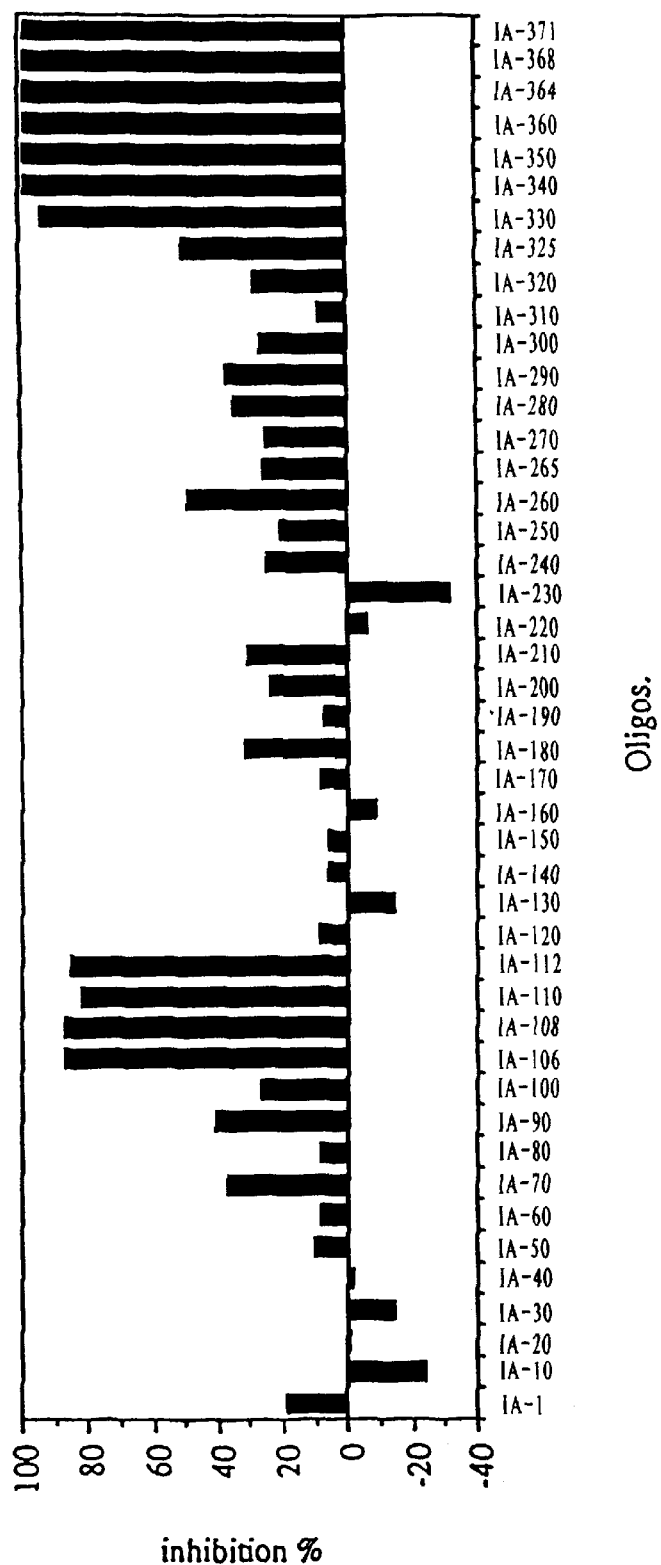
FIG. 8 is a bar graph showing results of a screen of phosphorothioate oligonucleotides by an in vitro translation assay after treatment with RNase H.

Because phosphorothioate oligonucleotides tended to show some degree of nonspecific inhibition of in vitro translation in the above assay, a number of phosphorothioates were rescreened in an assay in which RNase H treatment was carried out before the in vitro translation. 2.2 pmol RNA, 4.4 pmol antisense oligonucleotide and 0.23 units RNase H were combined in a total volume of 4 $\mu$l RNase H buffer consisting of 40 mM Tris HCl, pH 8.0, 20 mM MgCl$_2$, 200 mM KCl, and 10% sucrose. The reaction was carried out for 30 minutes at 37° C. In vitro translation and SDS-PAGE were carried out as described in previous examples. RNase H is activated to cleave target RNA only when oligonucleotide is hybridized to the RNA. Both P=O and P=S, but not 2'-O-methyl, oligonucleotides are able to activate RNAse H cleavage of RNA. RNA which has been cleaved is not translated into protein. Thus inhibition of translation in this assay indicates successful binding of oligonucleotide to target RNA. Randomized P=S control sequences did not show activity in this assay, demonstrating that they do not bind to the RNA target. Results are shown in FIG. 8.

Example 6

2'-O-propyl and Other Additional Oligonucleotides

Figure 9:
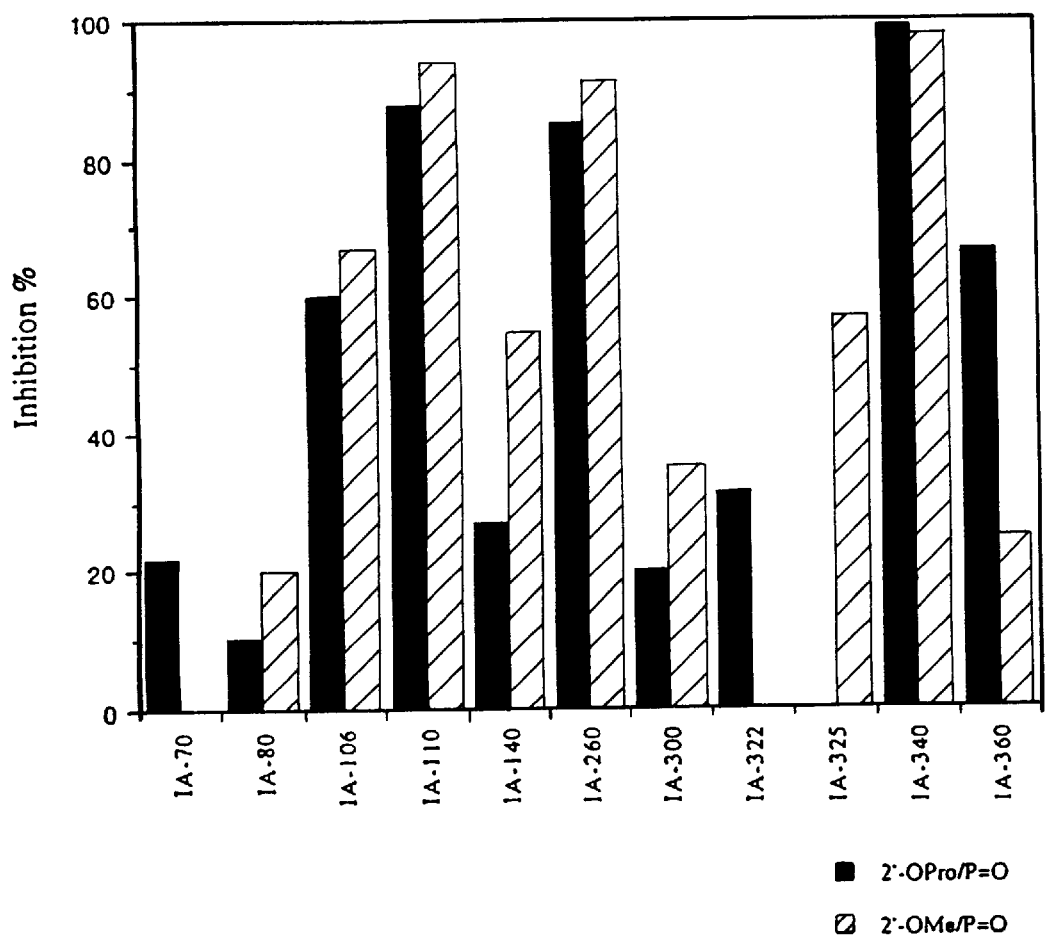
FIG. 9 is a bar graph showing inhibitory activities of 2'-O-propyl and 2'-O-methyl oligonucleotides.

The additional P=S, P=O and 2'-modified oligonucleotides (modified throughout) shown in Table 4 were synthesized. The 2'-O-propyl oligonucleotides were tested in the modified in vitro translation assay as in Example 5 and their activity compared to that of 2'-O-methyl oligonucleotides having the same sequence. As shown in FIG. 9, in most cases the 2'-O-propyl oligonucleotides were comparable in inhibition of HCV core protein translation to their 2'-O-methyl counterparts. Most active sequences were IA-110, IA-260 and IA-340; these are preferred embodiments of the invention. In the case of IA-360, the 2'-O-propyl oligonucleotide had greater inhibitory activity than the 2'-O-methyl version.

TABLE 4

Antisense oligonucleotides to HCV

| Oligo | Sequence | Location on HCV | Modifications | | | SEQ ID NO: |
|---|---|---|---|---|---|---|
| IA-1 | GCC CCG AAT CGG GGG CTG GC | 1–19 | P=S | P=O/2'-OMe | | 26 |
| IA-10 | TGG AGT GTC GCC CCC AAT CG | 10–29 | P=S | | | 27 |
| IA-20 | TGA TCT ATG GTG GAG TGT CG | 20–39 | P=S | P=O/2'-OMe | | 28 |
| IA-30 | CAC AGG GGA GTG ATC TAT GG | 30–49 | P=S | | | 29 |
| IA-40 | AGT AGT TCC TCA CAG GGG AG | 40–59 | P=S | P=O/2'-OMe | | 30 |
| IA-50 | GCG TGA AGA CAG TAG TTC CT | 50–69 | P=S | | | 31 |
| IA-60 | GAC GCT TTC TGC GTG AAG AC | 60–79 | P=S | P=O/2'-OMe | | 32 |
| IA-70 | GCC ATG GCT AGA CGC TTT CT | 70–89 | P=S | | P=O/2'-OPro | 33 |
| IA-80 | TCA TAC TAA CGC CAT GGC TA | 80–99 | P=S P=O | P=O/2'-OMe | P=O/2'-OPro | 34 |
| IA-90 | TGC ACG ACA CTC ATA CTA AC | 90–109 | P=S | | | 35 |
| IA-100 | TCC TGG AGG CTG CAC GAC AC | 100–119 | P=S | P=O/2'-OMe | | 36 |
| IA-106 | GGG GGG TCC TGG AGG CTG CA | 106–125 | P=S | P=O/2'-OMe | P=O/2'-OPro | 39 |
| IA-108 | AGG GGG GGT CCT GGA GGC TG | 108–127 | P=S | P=O/2'-OMe | | 40 |
| IA-110 | GGA GGG GGG GTC CTG GAG GC | 110–129 | P=S P=O | P=O/2'-OMe | P=O/2'-OPro | 41 |
| IA-112 | CGG GAG GGG GGG TCC TGG AG | 112–131 | P=S | P=O/2'-OMe | | 44 |
| IA-120 | GGC TCT CCC GGG AGG GGG GG | 120–139 | P=S | P=O/2'-OMe | | 48 |
| IA-130 | AGA CCA CTA TGG CTC TCC CG | 130–149 | P=S | | | 49 |
| IA-140 | CCG GTT CCG CAG ACC ACT AT | 140–159 | P=S P=O | P=O/2'-OMe | P=O/2'-OPro | 50 |
| IA-150 | GGT GTA CTC ACC GGT TCC GC | 150–169 | P=S | | | 51 |
| IA-160 | TGG CAA TTC CGG TGT ACT CA | 160–179 | P=S | P=O/2'-OMe | | 52 |
| IA-170 | CCG GTC GTC CTG GCA ATT CC | 170–189 | P=S | | | 53 |
| IA-180 | AAG AAA GGA CCC GGT CGT CC | 180–199 | P=S | P=O/2'-OMe | | 54 |
| IA-190 | GGG TTG ATC CAA GAA AGG AC | 190–209 | P=S | | | 55 |
| IA-200 | GGC ATT GAG CGG GTT GAT CC | 200–219 | P=S | P=O/2'-OMe | | 56 |
| IA-210 | CAA ATC TCC AGG CAT TGA GC | 210–229 | P=S | | | 57 |
| IA-220 | GGG GCA CGC CCA AAT CTC CA | 220–239 | P=S | P=O/2'-OMe | | 58 |
| IA-230 | CAG TCT CGC GGG GGC ACG CC | 230–249 | P=S | | | 59 |
| IA-240 | ACT CGG CTA GCA GTC TCG CG | 240–259 | P=S | P=O/2'-OMe | | 60 |
| IA-250 | ACC CAA CAC TAC TCG GCT AG | 250–269 | P=S | | | 61 |
| IA-260 | GCC TTT CGC GAC CCA ACA CT | 260–279 | P=S P=O | P=O/2'-OMe | P=O/2'-OPro | 62 |
| IA-265 | CAA GGC CTT TCG CGA CCC AA | 265–284 | P=S | P=O/2'-OMe | | 92 |
| IA-270 | GTA CCA CAA GGC CTT TCG CG | 270–289 | P=S | | | 63 |
| IA-280 | CTA TCA GGC AGT ACC ACA AG | 280–299 | P=S | P=O/2'-OMe | | 64 |
| IA-290 | CGC AAG CAC CCT ATC AGG CA | 290–309 | P=S | | | 65 |
| IA-300 | CCG GGG CAC TCG CAA GCA CC | 300–319 | P=S P=O | P=O/2'-OMe | P=O/2'-OPro | 66 |
| IA-310 | ACG AGA CCT CCC GGG GCA CT | 310–329 | P=S | | | 67 |
| IA-320 | TGC ACG GTC TAC GAG ACC TC | 320–339 | P=S | P=O/2'-OMe | | 68 |

TABLE 4-continued

Antisense oligonucleotides to HCV

| Oligo | Sequence | Location on HCV | Modifications | | | SEQ ID NO: |
|---|---|---|---|---|---|---|
| IA-322 | TGG TGC ACG GTC TAC GAG AC | 322–341 | | | P=O/2'-OPro | 69 |
| IA-325 | CAT GGT GCA CGG TCT ACG AG | 325–344 | P=S | P=O/2'-OMe | | 93 |
| IA-330 | GTG CTC ATG GTG CAC GGT CT | 330–349 | P=S | | | 73 |
| IA-340 | TTT AGG ATT CGT GCT CAT GG | 340–359 | P=S | P=O/2'-OMe | P=O/2'-OPro | 78 |
| IA-350 | TTC TTT GAG GTT TAG GAT TC | 350–369 | P=S | | | 86 |
| IA-360 | CGT TTG GTT TTT CTT TGA GG | 360–379 | P=S P=O | P=O/2'-OMe | P=O/2'-OPro | 91 |
| IA-364 | GTT ACG TTT GGT TTT TCT TT | 364–383 | P=S | P=O/2'-OMe | | 94 |
| IA-368 | TGG TGT TAC GTT TGG TTT TT | 368–387 | P=S | P=O/2'-OMe | | 95 |
| IA-371 | GGT TGG TGT TAC GTT TGG TT | 371–390 | P=S | P=O/2'-OMe | | 96 |

P=S: phosphorothioate; P=O: phosphodiester; 2'-O-Me: 2'-O-methyl; 2'-O-Pro: 2'-O-propyl Example 7

Evaluation of Oligonucleotides 120, 330 and 340 and Truncated Versions of Oligonucleotides 120, 260, 330 and 340 in H8Ad17 Cell Assay for Effects on HCV RNA Levels The anti-HCV activity of P=S oligonucleotides 120, 330 and 340 was evaluated in H8Ad17 cells as described in Example 4, except that instead of detecting and quantitating core protein, HCV RNA was isolated and quantitated by Northern blot analysis. As before, the oligonucleotide number is the number of the 5'-most nucleotide of the corresponding HCV RNA target sequence shown in the accompanying FIG. 1. For example, oligonucleotide 120 is a 20 mer targeted to nucleotides 120–139 of HCV RNA. Each of these compounds induced reduction in HCV RNA levels at doses of 0.5 $\mu$M and 0.17 $\mu$M. These three compounds (P=S 20 mers 120, 330 and 340) are therefore highly preferred. 15 mer versions (truncated at by 5 nucleotides at either the 3' or 5' end) induced a reduction of HCV RNA at the 0.5 $\mu$M dose. These compounds are therefore preferred. 10 mers did not show sequence-specific inhibition at either dose.

A number of shortened analogs of oligonucleotide 260 were synthesized as phosphorothioates and evaluated for effects on HCV RNA levels in the same assay. The sequence of oligonucleotide 260 was truncated at one or both ends. These oligonucleotides are shown in Table 5.

TABLE 5

| Oligo | Sequence | Activity % control | SEQ ID NO |
|---|---|---|---|
| 260 | 3'-TCA CAA CCC AGC GCT TTC GC -5' | 7% | 62 |
| | TCA CAA CCC AGC GCT TTC | 30% | 99 |
| | TCA CAA CCC AGC GCT TT | 30% | 100 |
| | TCA CAA CCC AGC GCT | 8% | 101 |
| | A CAA CCC AGC GCT TTC CG | 7% | 102 |
| | CAA CCC AGC GCT TTC CG | 7% | 103 |
| | A CCC AGC GCT TTC CG | 8% | 104 |
| | CA CAA CCC AGC GCT TTC C | 30% | 105 |
| | A CAA CCC AGC GCT TTC | 45% | 106 |

All of these oligonucleotides show good activity against HCV and are therefore preferred. Deletion of 5 nucleotides from either end of oligo 260 did not reduce inhibitory activity. Therefore, these 15 mers (SEQ ID NO: 101 and 104) are highly preferred. SEQ ID NOs 102 and 103 are also highly preferred. These results indicate that phosphorothioate oligonucleotides as short as 15 mers show excellent activity (reduction of HCV RNA expression). Based on these results, it is believed likely that even shorter oligonucleotides will be active. It is also believed that other modified oligonucleotides shorter than 15 nucleotides will be active.

A number of shortened analogs of oligonucleotide 330 were also synthesized as phosphorothioates and evaluated for effects on HCV RNA levels in the same manner. The sequence of oligonucleotide 330 was truncated at one or both ends. These oligonucleotides are shown in Table 6. Oligonucleotide concentration was 100 nM.

TABLE 6

| Oligo | Sequence | Activity % control | SEQ ID NO |
|---|---|---|---|
| 330 | GTG CTC ATG GTG CAC GGT CT | 30% | 73 |
| 9559 | GTG CTC ATG GTG CAC GGT | 53 | 108 |
| 9557 | GTG CTC ATG GTG CAC GG | 52 | 109 |
| 9558 | GTG CTC ATG GTG CAC G | 66 | 110 |
| 9036 | GTG CTC ATG GTG CAC | 37 | 111 |
| 9035 | GTG CTC ATG G | 100 | 112 |
| 10471 | G CTC ATG GTG CAC GGT CT | 27 | 113 |
| 10470 | CTC ATG GTG CAC GGT CT | 35 | 114 |
| 9038 | C ATG GTG CAC GGT CT | 32 | 115 |
| 9034 | TG CAC GGT CT | 82 | 116 |
| 10549 | TG CTC ATG GTG CAC GGT C | 17 | 117 |
| 10550 | G CTC ATG GTG CAC GGT | 36 | 118 |

In this assay, oligonucleotides 9036, 10471, 10470, 9038, 10549 and 10550 gave greater than 50% inhibition of HCV RNA expression and are therefore preferred.

Example 8

Evaluation of Oligos 259, 260 and 330 in the HCV H8Ad17 RNA Assay

The anti-HCV activity of P=S and 2'-O-propyl/P=S gapped oligonucleotides was evaluated in H8Ad17 cells as described in Example 7. P=S oligonucleotides 259, 260 and 330 all induced similar (approx 55%) reduction in HCV RNA levels in this assay, using 170 nM oligonucleotide concentration. The 2'-O-propyl gapped version of oligonucleotide 259 showed approximately 25% inhibition of HCV RNA levels (170 nM oligo dose), but oligonucleotides 260 and 330 were not active as 2'-O-propyl gapped oligonucleotides in this assay. In a previous assay of the same type, the gapped 2'-O-propyl version of oligonucleotide 330 did induce a reduction of HCV RNA, though less than was observed for the P=S 330 oligonucleotide.

Example 9

Evaluation of Oligos 259, 260 and 330 in an HCV H8Ad17 Protein Assay

A Western blot assay employing affinity-purified human polyclonal anti-HCV serum and $^{125}$I-conjugated goat anti-human IgG was developed in place of ELISA assays previously used to evaluate effects of oligonucleotides on HCV core protein levels. Six-well plates were seeded with H8 cells at 3.5×10$^5$ cells/well. Cells were grown overnight. Cells were treated with oligonucleotide in optimem containing 5 μg/ml lipofectin for 4 hours. Cells were fed with 2 ml H8 medium and allowed to recover overnight. To harvest cells, cells were washed once with 2 ml PBS, lysed in 100 μl Laemmli buffer and harvested by scraping. For electrophoresis, cell lysates were boiled, and 10–14 μl of cell lysate was loaded on each lane of a 16% polyacrylamide gel. After electrophoresing, proteins were transferred electrophoretically onto PVDF membrane. The membrane was blocked in PBS containing 2% goat serum and 0.3% TWEEN-20, and incubated overnight with primary antibody (human anti-core antibody 2243 and rabbit anti-G3PDH antibody). The membrane was washed 5×5 minutes in buffer, then incubated with secondary antibodies for 4–8 hours ($^{125}$I-conjugated goat anti-human, and $^{125}$I-conjugated goat anti-rabbit). The membrane was washed 5×5 minutes in buffer, sealed in plastic and exposed in a PhosphorImager cassette overnight. Bands were quantitated on the PhosphorImager (Molecular Dynamics, Sunnyvale Calif.), normalized to G3PDH expression levels, and results were plotted as a percentage of control untreated cells.

P=S and 2'-modified oligonucleotides 259, 260 and 330 were evaluated using this Western blot assay. These oligonucleotides are shown in Table 7. In the sequences shown, capital letters represent base sequence, small letters (o or s) represent internucleoside linkage, either phosphodiester (P=O) or phosphorothioate (P=S), respectively. Bold=2'-O-propyl. *=2'-O-butylimidazole. +=2'-O-propylamine.

TABLE 7

| Oligo # | Sequence | SEQ ID NO |
|---------|----------|-----------|
| 259 | CsCsTsTsTsCsGsCsGsAsCsCsCsAsAsCsAsCsTsA | 107 |
| 259 | CsCsTsTsTsCsGsCsGsAsCsCsCsAsAsCsAsCsTsA | 107 |
| 259 |   * *                            * *<br>CoCoToToToCoGoCoGoAoCoCoCoAoAoCoAoCoToA | 107 |
| 259 |   + +                            + +<br>CoCoToToToCoGoCoGoAoCoCoCoAoAoCoAoCoToA | 107 |
| 260 | GsCsCsTsTsTsCsGsCsGsAsCsCsCsAsAsCsAsCsT | 62 |
| 260 | GsCsCsTsTsTsCsGsCsGsAsCsCsCsAsAsCsAsCsT | 62 |
| 260 |   * *                            * *<br>GoCoCoToToToCoGoCoGoAoCoCoCoAoAoCoAoCoT | 62 |
| 260 |   + +                            + +<br>GoCoCoToToToCoGoCoGoAoCoCoCoAoAoCoAoCoT | 62 |
| 330 | GsTsGsCsTsCsAsTsGsGsTsGsCsAsCsGsGsTsCsT | 73 |
| 330 | GsTsGsCsTsCsAsTsGsGsTsGsCsAsCsGsGsTsCsT | 73 |
| 330 |   * *                            * *<br>GsTsGsCsTsCsAsTsGsGsTsGsCsAsCsGsGsTsCsT | 73 |
| 330 |   + +                            + +<br>GsTsGsCsTsCsAsTsGsGsTsGsCsAsCsGsGsTsCsT | 73 |

Cells were treated with oligonucleotide at doses of 25 nM, 100 nM or 400 nM. The greatest reduction in core protein (approx 90–95% at higher doses) was observed with P=S oligonucleotides 259, 260 and 330. These compounds are therefore highly preferred. 2'-O-propyl gapped P=S oligonucleotides 259, 260 and 330 showed >70%, >90% and approximately 80% inhibition of core protein expression, respectively. These compounds are therefore preferred. 2'-O-propyl/P=O compounds did not show activity in this assay.

Example 10

Synthesis of Oligos with 2'-O-propylamine or 2'-O-butylimidazole Chemical Caps

2'-O-propylamine nucleosides were synthesized from starting nucleosides as follows. 2'-O-phthalimidopropyl compounds are prepared from starting nucleosides in DMF by addition of dibutyltin oxide, tetrabutyl ammonium iodide and bromo-propyl phthalimide. The reaction flask is sealed and heated at 50° C. for 16 hours. The mixture is cooled and another portion of bromo-propyl phthalimide was added and the reaction heated for an additional 16 hours. At the end of this time, the reaction mixture is cooled to room temperature and diluted with methylene chloride and chromatographed using a methylene chloride/methanol gradient. The appropriate fractions are collected and concentrated. The corresponding DMTs are prepared by dissolving the resulting 2'-O-phthalimidopropyl compounds in dry pyridine and co-evaporating twice. The resulting foam is dissolved in dry pyridine and dimethoxytrityl chloride was added followed by 4,4-dimethylaminopyridine. The reaction is allowed to stir overnight at room temperature. Methanol is added to the reaction mixture and the solution is partitioned between saturated sodium bicarbonate and of chloroform. The aqueous layer is extracted with two additional portions of chloroform and the organic layers combined and dried with magnesium sulfate. After removal of the drying agent via filtration the filtrate is concentrated to an orange oil and purified by silica gel column chromatography using methanol/chloroform gradient with 0.5% pyridine added to neutralize the silica gel. Chloro-β-cyanoethoxy-N,N-diisopropylaminophosphine is added to the DMTs (in THF). The reaction mixture is stirred at room temperature for 20 hours. The reaction is concentrated and the residue purified by silica gel column chromatography. Elution with an ethyl acetate/hexane gradient while maintaining 1% triethylamine, pooling of appropriate fractions and evaporation gives the corresponding 2'-O-propylamine amidites.

Modified oligonucleotides were synthesized at a 10 μM scale and purified by HPLC reverse phase chromatography using a silica C18 reverse phase resin. Gradients were optimized for each chemistry to afford maximal purification and yield. Identity and purity of the final products were confirmed by PAGE, capillary gel electrophoresis (CGE) and electrospray mass spectrometry in accordance with methods well known in the art.

Oligonucleotides 259, 260 and 330 were synthesized as uniform 2'-O-propyl phosphodiester oligonucleotides with chemical caps added to two nucleotides at each end of the molecule. Caps were either 2'-O-propylamine or 2'-O-butylimidazole. Capping with two 2'-O-propylamine residues at the 3' end of an oligonucleotide results in significantly increased nuclease resistance. Capping of a phosphodiester (P=O) oligonucleotide with four 2'-O-butylimidazole residues was found to increase stability to snake venom phosphodiesterase by over eightyfold compared to the parent P=O compound. This is approximately fourfold more stable than the P=S compound.

2'-O-butylimidazole and 2'-O-propylamine capped compounds (oligos 259 and 260) showed approximately 40–50% inhibition at higher doses.

2'-O-butylimidazole and 2'-O-propylamine capped oligonucleotides 259, 260 and 330 were also tested in an in vitro translation assay as described in Example 2. HPLC-purified capped oligonucleotides demonstrated sequence-specific inhibitory activity in this assay, with activities comparable to or even more active than the parent phosphodiester oligonucleotide sequence. This indicates that these compounds are active against HCV protein expression.

Example 11

Evaluation of Shifted Variants of the 260 Sequence

Phosphorothioate oligonucleotides complementary to the nucleotide 254–289 region of the HCV genome were synthesized and evaluated for effects on HCV RNA levels. All compounds were 20 nucleotides in length and were shifted consecutively at two-base intervals, with the exception of oligonucleotide 259. The activities of these compounds are shown in Table 8. Effects of these oligonucleotides were evaluated in the H8Ad17 HCV RNA assay and expressed as percent of untreated control. All of the antisense oligonucleotides in the 254–289 region (oligonucleotides 254–270) induced 80–90% reductions in HCV RNA levels at doses of 170 nM. All of these oligonucleotides are therefore highly preferred, as are other oligonucleotides targeted to this preferred target region.

TABLE 8

| Oligo # | Activity (% of control) | SEQ ID NO |
|---|---|---|
| 254 | 17% | |
| 256 | 18% | |
| 258 | 18% | |
| 259 | 30% | 107 |
| 260 | 18% | 62 |
| 262 | 20% | |
| 264 | 17% | |
| 266 | 12% | |
| 268 | 10% | |
| 270 | 23% | 63 |
| 270scrambledcontrol | 100% at 500 nM dose | |

Example 12

Evaluation of Oligos in Cellular Assays (H8Ad17, Vaccinia)

Oligonucleotides 259, 260, 270, 275, 277, 330, 340, 345, 347, 350, 355 and 360 containing various modifications [P=S; 2'-O-propyl (uniform 2'-O-propyl or 2'-O-propyl gapped, both uniformly P=S); or 2'-fluoro modifications (gapped or uniform, both uniformly P=S)] were evaluated in HCV cellular assays, the H8Ad17 core protein Western blot assay. Results of the Western blot analysis are shown in Table 9. Where experiments were repeated, all results are given.

TABLE 9

Effect of modified oligonucleotides on
HCV core protein expression in H8Ad17 cells

| Oligo | Modif. | Activity (% of control expr) | SEQ ID NO |
|---|---|---|---|
| 259 | P=S | 27, 66 | 107 |
| 259 | Propyl gap | 100, 100 | 107 |
| 260 | P=S | 14, 9, 5, 11, 30, 29, 17, 22, 56 | 62 |
| 260 | Propyl gap | 58, 27 | 62 |
| 260 | Propyl | 100 62 | |
| 260 | Fluoro | 80, 38, 100 | 62 |
| 270 | P=S | 11, 22, 7, 31, 17, 8 | |
| 270 | Propyl gap | 87, 44, 80 | |
| 270 | Propyl | 67, 97 | |
| 270 | Fluoro gap | 27, 53 | |
| 270 | Fluoro | 100, 82, 83 | |
| 275 | P=S | 5 | |
| 277 | P=S | 6 | |
| 330 | P=S | 23, 33, 47, 36, 38, 6, 30 | 73 |
| 330 | Propyl gap | 38, 80 | 73 |
| 330 | Propyl | 100, 100 | 73 |
| 330 | Fluoro | 100, 100 | 73 |
| 330 | Fluoro gap | 48 | 73 |
| 340 | P=S | 28, 42, 61 | 78 |
| 340 | Propyl gap | 67 | 78 |
| 340 | Propyl | 82 | 78 |
| 340 | Fluoro | 35, 70, 23 | 78 |
| 345 | P=S | 44, 29 | |
| 345 | Propyl gap | 84 | |
| 345 | Propyl | 60 | |
| 345 | Fluoro | 20, 25, 48 | |
| 347 | Fluoro | 40 | |
| 350 | P=S | 67, 100 | 86 |
| 355 | P=S | 69, 89, 93 | |
| 355 | Fluoro | 22 | |
| 360 | P=S | 90, 52, 66 | 91 |
| 360 | Fluoro | 100, 87 | 91 |
| 360 | Propyl | 100 | 91 |
| 260 | scrambled P=S | 72 | |
| 270 | scrambled P=S | 100, 72 | |
| 330 | scrambled P=S | 100, 100 | |
| 340 | scrambled Propyl | 96 | |
| 340 | scrambled Fluoro | 98 | |

In this assay, the P=S oligonucleotides were consistently the best and are preferred. Of these, P=S oligonucleotides 260, 270, 275, 277 and 330 are more preferred. Uniform 2'fluoro P=S oligonucleotides 345, 347 and 355 are also more preferred.

Additional uniform 2'-fluoro phosphorothioate oligonucleotides were synthesized and tested for ability to inhibit HCV core protein expression. Oligonucleotide 344 was also found to be extremely active and is preferred. The region of the HCV RNA target from nucleotide 344 to nucleotide 374 was found to be extremely sensitive to antisense oligonucleotide inhibition. Oligonucleotides complementary to this target region, therefore, are preferred. More preferred among these are the 2'fluoro phosphorothioate oligonucleotides.

Example 13

Development of a Vaccinia Virus T7 Expression System for Evaluation of HCV Antisense Oligonucleotides Vaccinia virus was transfected with the construct used in Example 5, so that the HCV core gene and part of the env gene, behind a T7 promotor, was inserted in the TK gene. The virus was grown in CV-1 cells, and after homologous recombination was allowed to take place, recombinant vaccinia virus (TK−) was selected. This virus expresses the HCV sequence transcribed from the T7 promotor, and can be used to infect HepG2, RY5 or HeLa cells. HCV gene products are expressed at a very high level during vaccinia virus infection due to continuous synthesis of template DNA during vaccinia infection and high transcriptional efficiency of the T7 RNA polymerase. The nucleoside analog cytosine arabinonucleoside (Ara C) was used to inhibit viral DNA synthesis and thus limit production of template for RNA synthesis. Ara C was added to RY5 cells co-infected with vaccinia/HCV and vTF-7 (expressing the T7 RNA polymerase) recombinant viruses. RYS cells were pretreated for four hours with oligonucleotide 340 (20 mer P═S) or a scrambled version of the same, in the presence of 5 μg/ml lipofectin. Cells were refed with growth medium and incubated for 18–24 hours prior to infection with recombinant vaccinia viruses vTF-7 (expressing T7 RNA polymerase) and vNCE (vaccinia/HCV recombinant) at an m.o.i of 5.0. After a one-hour adsorption period, virus inoculum was aspirated and medium containing Ara C (0 to 500 ng/ml) was added to infected monolayers. RNA was extracted 8 hr after infection. Northern blot analysis showed that Ara C reduced HCV RNA transcripts to levels comparable to levels observed in H8Ad17 cells.

Example 14

Evaluation of a "Single Virus" Recombinant Vaccinia/HCV Core Protein Assay

A "single virus" vaccinia assay system was developed, which does not require co-infection with helper vaccinia virus expressing T7 polymerase. Cells were pretreated with oligonucleotide in the absence of lipofectin prior to infection with recombinant vaccinia virus expressing HCV sequences. Cells were then infected with recombinant vaccinia virus expressing HCV 5' UTR-core at a m.o.i. of 2.0 pfu/cell. After infection, cells were rinsed and post-treated with medium containing oligonucleotide. Initial results obtained with this assay indicate that P═S oligonucleotides 259 and 260 inhibit HCV 5'-UTR core expression by >60% at a concentration of 1 μM. Inhibition is dose-dependent.

Uniformly 2'-fluoro P═S oligonucleotides 260, 330 and 340 were evaluated for activity in the recombinant vaccinia "single virus" assay using RY5 cells. Medium containing oligonucleotide was added after infection. 2'-fluoro modified oligonucleotide 260 induced a dose-dependent inhibitory effect on HCV core protein expression (up to approximately 65% inhibition) even without pretreatment of cells with oligonucleotide before infection. In the same assay with pretreatment, 2'-fluoro P═S modified oligonucleotide 340 effectively inhibited HCV core protein expression at doses of 0.1 μM, 0.3 μM and 1.0 μM, with a maximum inhibition of about 75%. This oligonucleotide is therefore preferred. In the "single virus" assay using HepG2 cells, a dose-dependent inhibitory effect of oligonucleotide 340 as a uniform 2'-fluoro phosphorothioate was also observed (approximately 60% inhibition). This oligonucleotide is therefore preferred. The phosphorothioate oligonucleotide 260 also gave approximately 60% inhibition in the HepG2 cell assay.

Example 15

Recombinant Vaccinia/HCV-luciferase Assay

A recombinant vaccinia virus expressing HCV 5'UTR-core fused to firefly luciferase was developed. A foreign gene inserted into the vaccinia virus plasmid pSC11 is expressed from the vaccinia early/late promoter, P7.5. The plasmid also contains regions of the vaccinia virus thymidine kinase (TK) gene and the lac Z gene driven by the vaccinia P11 late promoter. The HCV 5' UTR, core and env coding sequences (HindIII to BamHI fragment excised from plasmid pGEMNCE) were inserted 5' of the firefly luciferase gene in pSC11. Vaccinia virus recombinants expressing HCV and luciferase were generated by transfection of cells followed by infection with wild-type virus. Recombinants were selected by β-galactosidase expression.

Oligonucleotide 260 was evaluated for activity in RY5 cells infected with a vaccinia/HCV-luciferase recombinant virus. Cells were pretreated with oligonucleotide for 4 hours (no lipofectin) and then infected with recombinant vaccinia virus VV-NCE-LUC at an m.o.i. of 5 pfu/cell. Cells were rinsed, refed with growth medium and incubated for 18–24 hours. Cell extracts were prepared in 60 μl luciferase assay buffer and 20 μl of extract was evaluated for luciferase activity using an automated luminometer. Results were quantitated and plotted as a percentage of untreated control cells. P═S oligonucleotide 260 gave approximately 65% inhibition of luciferase activity (i.e., inhibition of HCV core protein expression) at a concentration of 1 μM without lipofectin in this assay. A scrambled version of this sequence did not inhibit luciferase.

Example 16

Synthesis and Evaluation of Peptide-nucleic Acid (PNA) Oligonucleotide Analogs

PNA oligonucleotides were synthesized according to the procedure of Egholm et al., *J. Am. Chem. Soc.* 1992, 114, 1895; *J. Am. Chem. Soc.* 1992, 114, 9677. PNA oligonucleotides have been shown to possess greater nuclease resistance and stronger binding (measured as higher Tm) to complementary RNA target than their DNA (P═O or P═S) analogs. PNA oligonucleotide 340 (20 mer) had previously shown potent inhibition of HCV core protein translation in vitro. The 20 mer PNA oligonucleotide 340 was tested in this assay along with two 10 mers complementary to the same region (340–349 and 350–359) and 2'-O-methyl modified oligonucleotide 10 mers 343, 348 and 353. The PNA 20 mer 340 gave greater than 90% inhibition of core protein translation, while the 10 mer PNAs gave 70–80% inhibition. All of these PNA compounds are, therefore, preferred, with the 340 20 mer being more preferred. The 2'-O-methyl 10 mers gave maximum inhibition of 35% (oligo 343), 60% (348) and 80% (353). The 2'-O-methyl 10 mers 348 and 353 are therefore preferred, with 353 being more preferred.

Example 17

Synthesis and Evaluation of Oligonucleotide 260 with methylene(methylimino) (MMI) Internucleoside Linkages The introduction of MMI linkages into the oligonucleotide backbone has been shown to increase affinity of the oligonucleotide for its RNA target, and also to enhance nuclease resistance. The MMI linkage has also been shown to confer nuclease resistance to adjacent P═O linkages within an oligonucleotide. Vasseur et al., *J. Am. Chem. Soc.* 1992, 114, 4006–4007.

Oligonucleotides containing MMI linkages were synthesized according to the method of Vasseur et al., *J. Am. Chem. Soc.* 1992, 114:4006. Analogs of oligonucleotide 260 containing MMI backbone-substituted dimers (C-C, T-T or T-C dimers) were synthesized and purified by HPLC. These compounds, shown in Table 10, were evaluated in the H8Ad17 RNA and protein assays as in Examples 7 and 9.

TABLE 10

MMI analogs of oligonucleotide 260. Linkages marked with a * are MMI linkages. Other linkages are phosphorothioate (s) or phosphodiester (o)

| Oligo # | Sequence | SEQ ID NO |
|---|---|---|
| 10406 | 5'-GsC*CsT*TsT*CsGsCsGsAsCsC*CsAsAsCsAsCsT-3' | 62 |
| 10407 | GsC*CsT*TsT*CsGsCsGsAsCsCsCsAsAsCsAsCsT | 62 |
| 10408 | GsC*CoT*ToT*CsGsCsGsAsCsCsCsAsAsCsAsCsT | 62 |
| 10409 | GsC*CsTsT*TsCsGsCsGsAsCsCsCsAsAsCsAsCsT | 62 |
| 10410 | GsCsC*TsT*TsCsGsCsGsAsCsCsCsAsAsCsAsCsT | 62 |
| 10411 | GsCsC*ToT*TsCsGsCsGsAsCsCsCsAsAsCsAsCsT | 62 |
| 330 P=S | GsTsGsCTsCsAsTsGsGsTsGsCsAsCsGsGsTsCsT | 73 |
| 10900 | GsT*G$^{Me}$sC*TsCsAsTsGsGsTsGsCsAsCsGsGsTsCsT | 73 |
| 10899 | GoT*Go$^{Me}$C*TsCsAsTsGsGsTsGsCsAsCsGsGsTsCst | 73 |
| 350 P=S | TsTsCsTsGsAsGsGsTsTsTsAsGsGsAsTsTsC | 86 |
| 10897 | T*T$^{Me}$sC*TsTsT*GsAsGsGsTsT*TsAsGsAsTsT*C | 86 |
| 10898 | T*To$^{Me}$C*ToToT*GsAsGsGsTsT*TsAsGsAsTsT*C | 86 |
| 11048 | T*To$^{Me}$C*ToT*ToGoAoGoGoToT*ToAoGoGoAoToT*C | 86 |

In two assays evaluating the effects of these oligonucleotides in the H8Ad17 RNA assay, several MMI-modified compounds decreased HCV RNA to levels comparable to that achieved with P=S oligonucleotide 260. Compound 10409 reduced HCV RNA levels in both assays, to an even greater extent (85–90%) than did P=S 260 in this assay (55%). This compound is therefore highly preferred. The other MMI compounds having SEQ ID NO: 62 (targeted to nucleotides 260–279) all showed activity equal to or greater than the P=S 260 oligonucleotide in one or both assays. All of the compounds having SEQ ID NO: 62 shown in Table 10 are, therefore, preferred.

In the H8Ad17 core protein Western blot assay, oligonucleotides 10410 and 10411 showed activity comparable to P=S oligonucleotide 260 at the 100 nM and 400 nM doses. Oligonucleotide 10409 also reduced HCV core protein levels and was similar in activity to P=S oligonucleotide 260 at the 400 nM dose. Results from an assay at the 100 nM dose are given in Table 11.

TABLE 11

Activity of MMI oligonucleotides in H8Ad17 protein assay

| Oligo | Activity (% control) | SEQ ID NO: |
|---|---|---|
| 260 P = S | 10, 22 | 62 |
| 260 scrambled P = S | 73, 66 | 62 |
| 10406 | 82, 41 | 62 |
| 10407 | 57, 30 | 62 |
| 10408 | 56, 41 | 62 |
| 10409 | 39, 20 | 62 |
| 10410 | 10, 25 | 62 |
| 10411 | 6, 15 | 62 |

TABLE 11-continued

Activity of MMI oligonucleotides in H8Ad17 protein assay

| Oligo | Activity (% control) | SEQ ID NO: |
|---|---|---|
| 330 P = S | 30 | 73 |
| 10900 | 31 | 73 |
| 10899 | 17 | 73 |
| 350 P = S | 77 | 86 |
| 10897 | 47 | 86 |
| 10898 | 48 | 86 |
| 11048 | 100 | 86 |

MMI-containing oligonucleotides having SEQ ID NO: 73 (targeted to HCV RNA nucleotides 330–349) and SEQ ID NO: 86 (targeted to HCV RNA nucleotides 350–369), shown in Tables 10 and 11, were also found to be more active than phosphorothioate oligonucleotides having the same sequence, except for oligonucleotide 11048, which contained phosphorodiester linkages at all non-MMI positions and was inactive. These active compounds, therefore, are highly preferred.

Example 18

Identification of High Affinity Oligonucleotide Binding Sites in the 343–378 Region of the HCV Genome A combinatorial approach was used to identify optimum oligonucleotide binding sites on HCV RNA. A combinatorial (randomer) library of oligonucleotide 10 mers was hybridized to the HCV RNA target under conditions under which only high affinity binding sites are identified by RNAse H-mediated cleavage of the target at the site of oligonucleotide hybridization. Predominant RNAse H digestion products located between residues 29 and 38 of HCV RNA were found. Individual oligonucleotide 10 mers or 20 mers targeting the 29–38 region of HCV were evaluated to determine whether the observed RNAse H affinity cleavage products were the result of a high affinity oligo hybridizing to this region. Oligonucleotide association constants were determined using the single strand-specific, sequence-independent endoribonuclease RNAse One to footprint oligonucleotides bound to $^{32}$P-end-labeled HCV target RNA. The dissociation constants (Kd) measured for these oligonucleotides ranged from >$10^{-5}$ to $10^{-8}$M. Of the 10 mers studied, oligo 29 (targeted to nucleotides 29–38 of the HCV RNA) showed the greatest affinity for the RNA target. The Kd obtained for oligo 29 hybridizing to structured HCV RNA was approximately equal to the Kd obtained using an unstructured RNA 10 mer complement, indicating that this oligonucleotide is binding to both targets with equal affinities. This oligonucleotide is thereby defined to be an "optimal" binder for the structured RNA target.

Affinity values were also determined for 3 HCV antisense 20 mers that target the same region. The Kd values for the two best binders (20 mers targeted to nucleotides 24–43 and 29–48) indicated that they bound to the RNA target two to five times better than the best 10 mer oligonucleotide did.

RNAse H affinity cleavage assays using combinatorial oligonucleotide libraries have also been done for the 230–320 region of HCV RNA. Affinity sites were identified at nucleotides 275–277, 285 and 307–308.

The RNAse H oligonucleotide affinity mapping strategy was also applied to the core protein coding sequences of the HCV genome. HCV RNA was hybridized to a combinatorial library of oligonucleotide 10 mers (decamers) and optimal binding oligonucleotides were found. High affinity oligonucleotide binding sites on the HCV RNA target were identified by RNase H-mediated cleavage of the RNA target. The highest affinity sites were at nucleotides 365 (10 mer binding to nucleotides 365–374) and 357 (lo mer binding to nucleotides 357–366). A dissociation constant for each 10 mer oligonucleotide (vs. HCV target RNA) was determined by hybridization of each 10 mer to $^{32}$P-end labeled HCV RNA followed by RNAse One digestion. This value was compared to $1 \times 10^8$, the dissociation constant for a DNA 10 mer to a complementary RNA 10 mer. Oligonucleotide 365 yielded a Kd of $2 \times 10^8$ for binding to the structured HCV RNA target; this approximates the Kd for binding of a DNA 10 mer to the complementary RNA 10 mer. This, therefore, is an optimal binding oligonucleotide and is preferred. Oligonucleotide 357 yielded a Kd of $3 \times 10^7$, also close to the Kd for the short RNA target; this oligonucleotide is therefore also preferred. The 10 mer binding data suggest that the entire region from nucleotides 355–380 is a favorable site for oligonucleotide binding. This was confirmed by testing a series of DNA oligonucleotides from 10 to 20 nucleotides long, which bind to the region beginning at nucleotide 355. Binding of these oligos to the structured RNA target, compared to binding to a short complement, actually increased with oligonucleotide length, such that the 16 mer and 18 mer were nearly optimal. These oligonucleotides are, therefore, preferred, and the region of HCV RNA from nucleotide 355 to nucleotide 380 is highly preferred for targeting.

Using the nucleotide 355 oligonucleotides and varying both length and chemical modification, it was found that maximum length for best binding varied with molecule rigidity and affinity conferred by the modification. Thus, while 16 and 18 mer P=O oligonucleotides were nearly optimal binders, for phosphorothioates, a 20 mer was comparable and for phosphorothioate with uniform 2' fluoro modifications, a 14 mer was comparable. These results correlated well with activity of these oligonucleotides in the Western blot assay. These molecules are therefore preferred. These results indicate that shorter oligonucleotides which are modified or selected for their higher affinities can be used as effectively as longer oligonucleotides of lower affinities.

Example 19

Evaluation of Vaccinia/HCV/Luciferase Expression in Mice

Balb/c mice were inoculated intravenously ($1.6 \times 10^8$ pfu/mouse) or intraperitoneally ($4.8 \times 10^8$ pfu/mouse) with recombinant virus containing either HCV/luciferase sequences or just luciferase sequences. The viral constructs were those described in Example 15. Liver, spleen and kidney were harvested on day 2 or day 4 after inoculation, and evaluated for luciferase activity by luminometry of tissue homogenates. Regardless of means of administration, mice injected with recombinant virus expressing HCV and luciferase sequences died by day 4, whereas all mice injected with virus expressing only luciferase sequences were alive at day 4. Both mortality rate and luciferase expression will be used as endpoints to evaluate the effects of antisense oligonucleotides targeted to HCV in this system. Mice will be dosed intravenously by tail vein injection at doses of 20 mg/kg or 50 mg/kg. The first dose (pretreatment) will be given one day before viral inoculation, then again on day 0, four hours after inoculation. Subsequent doses will be on day 2 (for animals not sacrificed on day 2) and every two days thereafter as long as mice survive.

Example 20

Evaluation of HCV P=S Antisense Oligonucleotides in Chimpanzee

This study employed a chimpanzee chronically infected with HCV. The phosphorothioate oligonucleotide 260 was evaluated, and evaluation of phosphorothioate oligonucleotide 330 is in progress. Oligonucleotides of >90% purity were used, provided as a 10 mg/ml solution in PBS. Under storage conditions at 4–8° C. and protected from exposure to light, phosphorothioate oligonucleotides are stable for over 6 months. HCV RNA titers in serum samples taken from the chimp were determined by RT-PCR prior to start of treatment with oligonucleotide. The chimp selected for inclusion in the study had starting HCV RNA copy numbers of $10^4$–$10^5$, and weighed 37–39 kg. Compound was administered by slow I.V. infusion over a period of 2 hours. The animal was infused with compound at a dose of 4 mg/kg twice a week for the first two weeks, 6 mg/kg twice a week for the next two weeks, and 10 mg/kg twice a week for eight weeks (12 weeks total). Alternatively, animals can be dosed every other day with 2 mg/kg compound by intravenous bolus injection instead of infusion. The chimp was bled twice a week during these twelve weeks. RT-PCR will be used to determine HCV RNA titers in serum samples. Liver biopsies were also done weekly to check for pathology and will be evaluated to determine HCV RNA titers by RT-PCR.

Example 21

Diagnostic use of Oligonucleotides which Inhibit HCV

Definitive diagnosis of HCV-caused hepatitis can be readily accomplished using antisense oligonucleotides which inhibit HCV RNA function, measurable as a decrease in HCV RNA levels or HCV core protein levels. RNA is extracted from blood samples or liver tissue samples obtained by needle biopsy, and electrophoresed and transferred to nitrocellulose for Northern blotting according to standard methods routinely used by those skilled in the art. An identical sample of blood or tissue is treated with antisense oligonucleotide prior to RNA extraction. The intensity of putative HCV signal in the two blots is then compared. If HCV is present (and presumably causative of disease), the HCV RNA signal will be reduced in the oligonucleotide-treated sample compared to the untreated sample. If HCV is not the cause of the disease, the two samples will have identical signals. Similar assays can be designed which employ other methods such as RT-PCR for HCV RNA detection and quantitation, or Western blotting or ELISA measurement of HCV core protein translation, all of which are routinely performed by those in the art.

Diagnostic methods using antisense oligonucleotides capable of inhibiting HCV RNA function are also useful for determining whether a given virus isolated from a patient with hepatitis will respond to treatment, before such treatment is initiated. RNA is isolated from a patient's blood or a liver tissue sample and blotted as described above. An identical sample of blood or tissue is treated with antisense oligonucleotide to inhibit HCV prior to RNA extraction and blotting. The intensity of putative HCV signal in the two blots is then compared. If the oligonucleotide is capable of inhibiting RNA function of the patient-derived virus, the HCV signal will be reduced in the oligonucleotide-treated sample compared to the untreated sample. This indicates that the patient's HCV infection is responsive to treatment with the antisense oligonucleotide, and a course of therapeutic treatment can be initiated. If the two samples have identical signals the oligonucleotide is not able to inhibit replication of the virus, and another method of treatment is indicated. Similar assays can be designed which employ other methods such as RT-PCR for RNA detection and quantitation, or Western blotting or ELISA for quantitation of HCV core protein expression, all of which are routinely performed by those in the art.

Example 22

Inhibition of HCV Core Protein Expression by Uniformly Modified Oligonucleotides Oligonucleotides which are uniformly substituted at the 2' position do not serve as substrates for RNAse H, a cellular endonuclease that cleaves the RNA strand of RNA:DNA duplexes. Chemical modification of antisense oligonucleotides at the 2' position has been shown to increase duplex stability and can enhance resistance of the oligonucleotide to nucleolytic degradation. 2'-methoxyethoxy modification of phosphodiester oligonucleotides increases their nuclease resistance to a level similar to that of deoxyphosphorothioates and also increases hybridization affinity.

Inhibition of HCV core protein expression by fully 2'-methoxyethoxy oligonucleotides was evaluated. 2'-methoxyethoxy/P=O analogs of SEQ ID NOs: 62, 73 and 78 were synthesized and tested. Cells treated with ISIS 11155, the 2'-methoxyethoxy/P=O oligonucleotide having SEQ ID NO: 78, showed a concentration-dependent reduction in HCV core protein expression. The activity of this compound was greater than that of a deoxyphosphorothioate oligonucleotide of the same sequence. An IC50 for the 2'methoxyethoxy/P=O analog of SEQ ID NO: 78 was calculated to be less than 62 nM. A 2'methoxyethoxy/P=O scrambled control oligonucleotide did not inhibit HCV core protein expression. Treatment of H8Ad17c cells with ISIS 11155, the 2'-methoxyethoxy/P=O oligonucleotide having SEQ ID NO: 78, did not reduce HCV RNA levels suggesting the observed inhibition of core protein synthesis did not depend on activation of RNAse H.

What is claimed is:

1. An oligonucleotide selected from the group consisting of SEQ ID NO: 41, SEQ ID NO: 38, SEQ ID NO: 39, SEQ ID NO: 40, SEQ ID NO: 44, SEQ ID NO: 45, SEQ ID NO: 48, SEQ ID NO: 81, SEQ ID NO: 82, SEQ ID NO: 87, SEQ ID NO: 88, SEQ ID NO: 89, and SEQ ID NO: 90.

2. The oligonucleotide of claim 1 which comprises at least one 2' fluoro modification.

3. The oligonucleotide of claim 1 which comprises at least one modified intersugar linkage.

4. The oligonucleotide of claim 3 wherein the intersugar linkage is a phosphorothioate, PNA or methylene (methylimino) linkage.

5. The oligonucleotide of claim 1 which comprises an —O-alkyl or fluoro modification at the 2'-position of at least one sugar moiety.

6. The oligonucleotide of claim 1 having a universal base at a position which is complementary to a nucleotide in the HCV RNA which is variable among strains of HCV.

7. The oligonucleotide of claim 6 wherein the universal base is inosine.

8. A method for inhibiting the activity of a Hepatitis C virus comprising contacting the virus or cells infected with the virus with an effective amount of an oligonucleotide of claim 1 so that function of a Hepatitis C virus RNA is inhibited.

* * * * *